(12) United States Patent
Braiman-Wiksman et al.

(10) Patent No.: US 7,638,484 B2
(45) Date of Patent: Dec. 29, 2009

(54) METHODS FOR ACCELERATING WOUND HEALING BY ADMINISTRATION OF ADIPOKINES

(75) Inventors: Liora Braiman-Wiksman, Rishon-LeZion (IL); Inessa Solomonik, Ganei-Tikva (IL)

(73) Assignee: Healor Ltd., Ness Ziona (IL)

( * ) Notice: Subject to any disclaimer, the term of this patent is extended or adjusted under 35 U.S.C. 154(b) by 16 days.

(21) Appl. No.: 11/348,527

(22) Filed: Feb. 7, 2006

(65) Prior Publication Data
US 2006/0177418 A1    Aug. 10, 2006

Related U.S. Application Data

(63) Continuation-in-part of application No. PCT/IL2004/000727, filed on Aug. 5, 2004.

(60) Provisional application No. 60/493,000, filed on Aug. 7, 2003.

(51) Int. Cl.
*A61K 38/00*   (2006.01)
*C07K 1/00*   (2006.01)

(52) U.S. Cl. .......................................... 514/2; 530/351

(58) Field of Classification Search .................. None
See application file for complete search history.

(56) References Cited

U.S. PATENT DOCUMENTS

| | | | |
|---|---|---|---|
| 4,673,649 A | 6/1987 | Boyce et al. | |
| 4,833,257 A | 5/1989 | Pettit et al. | |
| 4,940,660 A | 7/1990 | Hirai | |
| 5,145,679 A | 9/1992 | Hinson | |
| 5,444,041 A | 8/1995 | Owen et al. | |
| 5,461,030 A | 10/1995 | Lindenbaum | |
| 5,591,709 A | 1/1997 | Lindenbaum | |
| 5,723,119 A * | 3/1998 | Schwarz et al. | 424/85.2 |
| 5,770,228 A | 6/1998 | Edwards et al. | |
| 5,869,037 A | 2/1999 | Crystal et al. | |
| 5,942,487 A | 8/1999 | Ogawa et al. | |
| 5,981,606 A | 11/1999 | Martin | |
| 6,028,118 A | 2/2000 | Dupont et al. | |
| 6,096,288 A | 8/2000 | Roth | |
| 6,319,907 B1 | 11/2001 | Ferguson | |
| 6,403,656 B1 | 6/2002 | Rivier | |
| 6,485,721 B1 | 11/2002 | Yoshida et al. | |
| 6,489,306 B2 | 12/2002 | Mohapatra et al. | |
| 6,541,447 B1 | 4/2003 | Dawson | |
| 6,582,713 B2 | 6/2003 | Newell et al. | |
| 6,737,241 B2 | 5/2004 | Nolan | |
| 6,841,472 B2 | 1/2005 | Mayuzumi | |
| 7,074,408 B2 | 7/2006 | Fanslow et al. | |
| 7,261,881 B1 * | 8/2007 | Sierra-Honigmann | 424/85.1 |
| 2001/0036955 A1 | 11/2001 | Gerritsen et al. | |
| 2002/0119914 A1 | 8/2002 | Zhu et al. | |
| 2003/0144180 A1 | 7/2003 | Tennenbaum et al. | |
| 2003/0147855 A1 * | 8/2003 | Zolotukhin et al. | 424/93.2 |
| 2004/0175384 A1 | 9/2004 | Mohapatra et al. | |
| 2005/0054608 A1 | 3/2005 | Linge et al. | |
| 2006/0177443 A1 | 8/2006 | Fanslow et al. | |
| 2008/0182780 A1 | 7/2008 | Linge et al. | |

FOREIGN PATENT DOCUMENTS

| | | |
|---|---|---|
| EP | 0 561 330 | 9/1993 |
| EP | 0 679 402 | 2/1995 |
| GB | 0 280 460 | 8/1998 |
| GB | 2 369 572 | 6/2002 |
| RU | 2 115 410 C1 | 7/1998 |
| WO | WO 85/05036 | 11/1985 |
| WO | WO 89/10129 | 11/1989 |
| WO | WO 90/11071 A1 | 10/1990 |
| WO | WO 92/18147 | 10/1992 |
| WO | WO 93/04691 A | 3/1993 |
| WO | WO 93/25660 A1 | 12/1993 |
| WO | WO 96/09810 | 4/1996 |
| WO | WO 96/20724 | 7/1996 |
| WO | WO 96/23522 | 8/1996 |
| WO | WO 99/18920 | 4/1999 |
| WO | WO 99/35283 | 7/1999 |
| WO | WO 99/53943 | 10/1999 |
| WO | WO 00/30628 | 6/2000 |
| WO | WO 01/76650 | 10/2001 |
| WO | WO 02/17980 A2 | 3/2002 |
| WO | WO 02/43751 | 6/2002 |
| WO | WO 02/009639 | 7/2002 |
| WO | WO 02/072092 A1 | 9/2002 |
| WO | WO 02/087576 A1 | 11/2002 |
| WO | WO 02/094877 | 11/2002 |
| WO | WO 2005/007072 | 1/2005 |
| WO | WO 2007/075911 A2 | 7/2007 |

OTHER PUBLICATIONS

U.S. Appl. No. 09/169,801, filed Aug. 1, 2000, Roth.
Rangwala and Lazar, Adipogenic Transcriptional Regulation, Annu. Rev. Nutr. 2000, 20, 535-559.

(Continued)

*Primary Examiner*—Robert Landsman
*Assistant Examiner*—Gyan Chandra
(74) *Attorney, Agent, or Firm*—Fulbright & Jaworski L.L.P.

(57) ABSTRACT

Methods for inducing or accelerating a healing process of a damaged skin or skin wounds are described. The methods include administering to the skin cells colonizing the damaged skin or skin wound a therapeutically effective amount of an adipokine, an adipocyte or preadipocyte modulator, adipocytes, preadipocytes, or stem cells, or transforming the skin cells colonizing the damaged skin or skin wound such as to express and secrete an adipokine, thereby inducing or accelerating the healing process of the damaged skin or skin wound.

14 Claims, 12 Drawing Sheets

OTHER PUBLICATIONS

Michalik et al., Impaired skin wound healing in perioxisome proliferator-activated receptor (PPAR) and PPAR mutant mice, J. Cell Biol. 2001, 154, 799-814.

Frank, et al. "Leptin enhances wound re-epithelialization and constitutes a direct function of leptin in skin repair", *J. Clin. Investigation*, vol. 106, No. 4 (2000), pp. 501-509.

Traverso, et al. "Immunological evidence for increased oxidative stress in diabetic rats", *Diabetologia* (1998) 41: 265-170.

Al, et al. "The experimental study of bone marrow mesenchymal stem cells on the repair of skin wound combined with local radiation injury", *Zhonhghua Yi Xue Za Zhi*, 82(23), (2002), pp. 1632-1636; Pubmed Abstract PMID 12667374.

Alessenko, et al. "Selective changes in protein kinase C isoenzymes in rat liver nuclei during liver regeneration", *Biochem. Biophys, Commun.*, 182, (1992), pp. 1333-1339.

Andre, et al. "Protein kinases C-gamma and -delta are involved in insulin-like growth factor I-Induced migration of colonic epithelial cells", *Gastroent.* 116(1) (1999), pp. 64-77.

Bajou, et al. "Absence of host plasminogen activator inhibitor 1 prevents cancer invasion and vascularization", *Nat. Med.*, 4 (1998), pp. 923-928.

Bandyopadhyay, et al. "Effects of transiently expressed atypical ($\zeta$, $\Lambda$), conventional ($\alpha$, $\beta$) and novel ($\delta$, $\epsilon$) [..]", *Biochem. J.*, 337 (1999), pp. 461-470.

Benes, et al. "The C2 domain of PKC $\delta$ is a phosphotyrosine binding domain", *Cell*, 121 (2005), pp. 271-280.

Bitar, et al. "Insulin and glucocorticoid-dependent suppression of the IGF-I system I diabetic wounds", *Surgery*, 127(6) (2000), pp. 687-695.

Braiman, et al. "Tyrosine phosphorylation pf specific protein kinase C izoenzymes participates in insulin stimulation of glucose transport in primary cultures of rat skeletal muscle", *Diaetes*, 48(10) (1999), pp. 1922-1929.

Braiman, et al. "Protein Kinase C$\delta$ Mediates Insulin-Induced Glucose Transport in Primary Cultures of Rat Skeletal Muscle", *Endocrin.*, 13(12), pp. 2002-2012, 2000.

Chida, et al. "The $\eta$ isoform of protein kinase C is localized on rough endoplasmic reticulum", *Mol. Cell Biol.* 14 (1994), pp. 3782-3790.

Denning, et al. "Specific protein kinase C isozymes mediate the induction of keratinocyte differentiation markers by calcium", *Cell Growth Differ.*, 6 (1995), pp. 149-157.

Dlugosz and Yuspa "Coordinate changes in gene expression which mark the spinous to granular call transition in epidermis are regulated by protein kinase C", *J. Cell. Biol.*, 120 (1993), pp. 217-225.

Ferber, et al. "Pancreatic and duodenal homeobox gene 1 induces expression of insulin genes in liver and ameliorates [..]", *Nature Med.* 6(5) (2000) pp. 568-572.

Formisano, et al. "In NIH-3T3 fibroblasts, insulin receptor interaction with specific protein kinase C isoforms controls receptor intracellular routing", *J. Biol, Chem.*, 273 (1998), pp. 12197-13202.

Gcshwendt "Protein kinase C$\delta$", *Eur. J. Biochem.*, 259 (1999), pp. 555-564.

Hengge, et al. "Epidermis as target for in vivo gene-therapy", *J. Invest. Dermatol.* 105(3) (1995) p. 448.

Hofmann "The potential for isoenzyme-selective modulation of protein kinase C", *The FASEB J.*, 11 (1997), pp. 649-669.

Jeschke, et al. "IGF-I gene transfer in thermally injured rats", *Gene Ther.*, 6(6) (1999), pp. 1015-1020.

Jeschke, et al. "Effect of multiple gene transfer of insulinlike growth factor I complementary DNA gene constructs in rats after thermal injury", *Arch. Surg.*, 134(10) (1999), pp. 1137-1141.

Lindenbaum, et al. "Serum-free culture medium induces acceleration of wound healing in guinea-pigs", *Burns*, 21(2) (1995), pp. 110-115.

MacFarlane, et al. "Glucose stimulates translocation of the homeodomain of transcription factor PDX1 from the cytoplasm to the nucleus of pancreatic bet-cells", *J. Biol. Chem.*, 274(2), (1999), pp. 1001-1016.

Madibally, et al. "Influence of insulin therapy on burn wound healing in rats", *J. Surg. Res.*, 109 (2003), pp. 92-100.

Mischak, et al. "Phorbol ester- induced myeloid differentiation is mediated by protein kinase C-$\alpha$ and -$\delta$ and not by protein kinase C-$\beta$II, -$\epsilon$, -E, and -$\eta$", *J. Biol. Chem.*, 268 (1993), pp. 20110-20115.

Mischak, et al. "Overexpression of Protein Kinase C-$\delta$ and -$\epsilon$ in NIH 3T3 Cells Induces Opposite Effects [..]", *J. Biol. Chem.*, 268(9), (1993), pp. 6090-6096.

Mooney, et al. "Tumor necrosis factor and wound healing", *Annals of Surgery*, 211 (2), (1990) pp. 124-129.

Ohba, et al. "Induction of differentiation in normal human keratinocytes by adenovirus-mediated introduction [..]", *Mol. Cel. Biol.*, 18(9)(1998), pp. 5199-5207.

Osada, et al. "A phorbol ester receptor/protein kinase [..]", *J. Biol. Chem.*, 265 (1990), pp. 22434-22440.

Pellegrini, et al. "Cultivation of human keratinocyte stem, cells: current and future clinical applications", *Med. Biol. Eng. Comp.* 36(6), (1998), pp. 778-790.

Perletti, et al. "Protein Kinase C$\epsilon$ is oncogenic in colon epithelial cell s by interaction with the *ras* signal transduction pathway", *Oncogene* 16 (1998), pp. 3345-3348.

Pittelkow, et al. "Serum-free culture of normal human melanocytes: growth kinetics and growth factor requirements", *J. Cel. Physiol.*, 140(3) (1989), pp. 565-576.

Reynolds, et al. "Down-regulation of langerhans cell protein kinase C-beta isoenzyme expression in inflammatory and hyperplastic dermatoses", *Br. J. Dermatol.*, 133(2), (1995), pp. 157-167 [PMED Abstract 7547380].

Ring, et al. "Systematically and topically administered leptin both accelerate wound healing in diabetic *ob/ob* mice", *Endocrin.*, 141(1), (2000), pp. 446-449.

Servold, et al., "Growth factor impact on wound healing", *Clinics in Pod. Med. Surg.*, 8(4), (1991), pp. 937-953.

Setoguchi, et al. "Ex vivo and in vivo gene transfer to the skin using replication-deficient recombinant adenovirus vectors", *J. Invest. Dermatol.* 102(4) (1994) pp. 415-421.

Shen, et al., "Protein Kinase C activation: a divergence point in the signaling of insulin and insulin like growth factor-1 induced proliferation of skin keratinocytes", Bar Illan Univ., Ramat Gan, Israel (Abstract), Apr. 2000.

Soltoff and Toker "Carbachol, substance P, and phorbol ester promote the tyrosine phosphorylation of protein kinase C$\delta$ in salivary gland epithelial cells", *J. Biol. Chem.*, 270 (1995), pp. 13490-13495.

Spravchikov, et al., "The interactive effects of hyperglycemia, insulin and IGF-1 in murine skin cells—an IR-null mouse model", Dept. of Pathol., Sackler School of Medicine, Tel Aviv Univ., Israel (Abstract), Aug. 2000.

Spravchikov, et al., "Glucose effects on skin keratinocytes: implications for diabetes skin complications", *Diabetes*, 50(7) (2001), pp. 1627-1635.

Sun, et al. "Squamous metaplasia of normal and carcinoma in situ of HPV 16-immortalized human endocervical cells", *Cancer Res.*, 52 (1992), pp. 4254-4260.

Taran, et al. "Improved vitality of experimental random dorsal skin flaps in rats treated with enriched cell culture medium", *Plast. Reconstr. Surg.*, 104(1) (1999), pp. 148-151.

Tennebaum, et al. "Selective changes in laminin adhesion and $\alpha_6\beta_4$ integrin regulation are associated with the initial steps in keratinocyte maturation", *Cell Growth Differ.*, 7 (1996), pp. 615-628.

Wang, et al. "Differential localization of protein kinase C $\delta$ by phorbol esters and related compounds using a fusion protein with green fluorescent protein", *J. Biol. Chem.*, 274 (1999), pp. 37233-37239.

Wertheimer, et al., "The effects of insulin signaling on skin proliferation and differentiation—lessons from the IR- and IRS1 Null Models", Dept. of Pathol., Sackler School of Medicine, Tel Aviv Univ., Israel (Abstract), Aug. 2000.

Wertheimer, et al. "Differential roles of insulin receptor and insulin-like growth factor-1 receptor I differentiation of murine skin keratinocytes", *J. Invest. Dermatol.*, (2000), pp. 24-29.

Werthimer, et al. "The regulation of skin proliferation and differentiation in the IR null mouse: implications for skin complications of diabetes", *Endocrin.*, 142(3) (2001), pp. 1234-1241.

Yuspa "The pathogenesis of squamous cell cancer: lessons learned from studies of carcinogenesis", *Cancer Res.*, 54 (1994), pp. 1178-1189.

Belfield, et al.: "The use of Insulin in open-wound healing", from a paper presented at 81st Annual Convention of the California Veterinary Medical Association Oct. 3, 1969.

Greenway, et al.: "Topical insulin in wound healing: a randomised, double-blind, placebo-controlled trial", *J. Wound Care*, vol. 8, No. 10 (1999) pp. 526-528.

http://www.drugs.com/pdr/lletin_II.html Information for patient, Aug. 4, 2006.

Kirton: Presentation at Symposium Keloids and Hypertrophic Scars, Grand Rounds, Oct. 1999; http://www.uic.edu/depts/doms/rounds/rounds-35.html.

Lesion definition: http://216.251.232.159/semdweb/internetsomd/ASP/1533197.asp.

Anonymous "Dulbecco's Phosphate Buffered Saline (D-PBS)", Internet Article Abstact from URL:http://www.hyclone.com/media/dulbeccos_phosphate.htm>.

Braiman-Wiksman, et al. "Novel Insights into Wound Healing Sequence of Events", *Toxicologic Pathology*, GB, vol. 35, No. 6, (2007), pp. 767-779.

Cataisson, et al. "Activation of Cutaneous Protein Kinase Cα Induces Keratinocyte Apoptosis and Intraepidermal Inflammation by Independent Signaling Pathways", *J. of Immunol.*, US, vol. 171, No. 5, (2003), pp. 2703-2713.

Jones, et al. "Staurosporine, a non-specific PKC inhibitor, induces keratinocyte differentiation and raises intracellular calcium, but Ro31-8220, a specific inhibitor does not", *J. of Cell. Physiol.*, vol. 159, No. 2, (1994), pp. 324-330; Abstract XP-002520100, Database EMBASE [Online], Elsevier Science Publishers, Amsterdam, NL (1994).

Liao, et al. "Effect of α-Protein Kinase C Neutralizing Antibodies and the Pseudosubstrate Peptide on Phosphorylation, Migration, and Growth of REF52 Cells", *Cell Growth and Differentiation*, vol. 4, No. 4, (1993), pp. 309-316.

Papp, et al. "Protein kinase C isozymes regulate proliferation and high cell density-mediated differentiation in HaCaT keratinocytes", *Experim. Dermatol.*, GB, vol. 12, No. 6, (2003) pp. 811-824.

Pierre, et al. "Effects of Insulin on Wound Healing", *J. of Trauma*, US, vol. 44, No. 2 (1998), pp. 342-345.

Shen, et al. "A Divergence Point in the Signaling of Insulin and IGF-1-Induced Proliferation of Skin Keratinocytes", *Diabetes*, US, vol. 50, No. 2 (2001), pp. 255-264.

Stanwell, et al. "Staurosporine induces a complete program of terminal differentiation in neoplastic mouse keratinocytes via activation of protein kinase C", *Carcinogenesis*, GB, (1996), vol. 17, No. 6, pp. 1259-1265.

Varker, et al. "Involvement of the muscarinic acetylcholine receptor in inhibition of cell migration", *Biochem. Pharmocol.*, US, vol. 63, No. 4, (2002), pp. 597-605.

Wallis, et al. "The α Isoform of Protein Kinase C Is Involved in Signaling the Response of Desmosomes to Wounding in Cultured Epithelial Cells", *Molecular Biol. Of the Cell*, US, vol. 11, No. 3, (2000), pp. 1077-1092.

Yuspa, et al. "Expression of Murine Epidermal Differentiation Markers Is Tightly Regulated by Restricted Extracellular Calcium Concentrations In Vitro", *J. of Cell Biol.*, US, vol. 109, No. 3, (1989), pp. 1207-1217.

Cordeiro "Beyond mitomycin: TGF-β and wound healing", *Progress and Eye Res.* 21 (2002) 75-89.

Di Peppe, et al. "Adenovirus-mediated $VEGF_{165}$ gene transfer enhances wound healing by promoting angiogenesis in CD1 diabetic mice", *Gene Therapy*, (2002) 9, 1271-1277.

Volevodz, et al. "STH and IGF-I in case of diabetes mellitus: their role in pathogenesis of microvascular complications" (2000) http://www.diabet.ru/Sdiabet/2000-01/2000-01-13.htm.

Yuli "Innovative PKC modulating formulation dramatically improves the healing of diabetic wounds", *J. Investigative Dermat.* Abstract 290, XP009121582, p. A49,vol. 122, No. 3 (2004).

* cited by examiner

Control

PPAR gamma antagonist (GW9662)

Adipsin

Control

Insulin

Ins+PPARγ agonist (troglitazone)

PPARγ agonist (troglitazone)

METHODS FOR ACCELERATING WOUND HEALING BY ADMINISTRATION OF ADIPOKINES

CROSS-REFERENCE TO RELATED APPLICATIONS

The present application is a continuation-in-part application of PCT application No. PCT/IL2004/000727, filed Aug. 5, 2004, in which the US is designated, and claims the benefit of U.S. Provisional Patent Application No. 60/493,000, filed Aug. 7, 2003, now expired, the entire contents of each and both these applications being hereby incorporated by reference herein in their entirety as if fully disclosed herein.

FIELD AND BACKGROUND OF THE INVENTION

The present invention relates to methods and pharmaceutical compositions for inducing and/or accelerating cell proliferation and/or cell migration and/or cell differentiation and thereby accelerating the healing process of wounds. More particularly, the present invention relates to the use of bioactive molecules which are secreted by adipocytes (adipokines), and bioactive molecules which modulate adipocytes and preadipocytes differentiation, and/or adipocytes proliferation and/or activity and/or chemotaxis, for inducing or accelerating the healing process of a damaged skin or skin wound.

The primary goal in the treatment of wounds is to achieve wound closure. Open cutaneous wounds represent one major category of wounds and include surgical wounds, burn wounds, neuropathic ulcers, pressure sores, venous stasis ulcers, and diabetic ulcers.

Open cutaneous wounds routinely heal by a process that comprises six major components: (i) inflammation; (ii) fibroblast proliferation; (iii) blood vessel proliferation; (iv) connective tissue synthesis; (v) epithelialization; and (vi) wound contraction. Wound healing is impaired when these components, either individually or as a whole, do not function properly. Numerous factors can affect wound healing, including malnutrition, infection, pharmacological agents (e.g., actinomycin and steroids), advanced age and diabetes (Hunt and Goodson, 1988).

With respect to diabetes, diabetes mellitus is characterized by impaired insulin signaling, elevated plasma glucose and a predisposition to develop chronic complications involving several distinctive tissues. Among all the chronic complications of diabetes mellitus, impaired wound healing leading to foot ulceration is among the least well studied. Yet skin ulceration in diabetic patients takes a staggering personal and financial cost (Knighton and Fiegel, 1993; Shaw and Boulton, 1997). Moreover, foot ulcers and the subsequent amputation of a lower extremity are the most common causes of hospitalization among diabetic patients (Shaw and Boulton, 1997; Coghlan et al., 1994; Grunfeld, 1992; Reiber et al., 1998). In diabetes, the physiological process of wound healing is impaired. The defect in tissue repair has been related to several factors including neuropathy, vascular disease and infection. However, other mechanisms whereby the diabetic state associated with abnormal insulin signaling impairs wound healing and alters the physiology of skin has not been elucidated.

Another issue associated with impaired wound healing relates to infections of post surgical wounds occurring in 25% of patients hospitalized in surgical wards.

Skin is a stratified squamous epithelium in which cells undergoing growth and differentiation are strictly compartmentalized. In the physiologic state, proliferation is confined to the basal cells that adhere to the basement membrane. Differentiation is a spatial process where basal cells lose their adhesion to the basement membrane, cease DNA synthesis and undergo a series of morphological and biochemical changes. The ultimate maturation step is the production of the cornified layer forming the protective barrier of the skin (Hennings et al., 1980; Yuspa et al., 1989). The earliest changes observed when basal cells commit to differentiate is associated with the ability of the basal cells to detach and migrate away from the basement membrane (Fuchs, 1990). Similar changes are associated with the wound healing process where cells both migrate into the wound area and proliferative capacity is enhanced. These processes are mandatory for the restructuring of the skin layers and induction of proper differentiation of the epidermal layers.

The analysis of mechanisms regulating growth, differentiation and migration of epidermal cells has been greatly facilitated by the development of culture systems for mouse and human keratinocytes (Yuspa et al., 1989; Yuspa, 1994). In vitro, keratinocytes can be maintained as basal proliferating cells with a high growth rate. Furthermore, differentiation can be induced in vitro following the maturation pattern in the epidermis in vivo. The early events include loss of hemidesmosome components (Fuchs, 1990, Hennings and Holbrook, 1983) and a selective loss of the $\alpha 6\beta 4$ integrin and cell attachment to matrix proteins. This suggests that changes in integrin expression are early events in keratinocyte differentiation. The early loss of hemidesmosomal contact leads to suprabasal migration of keratinocytes and is linked to induction of Keratin 1 (K1) in cultured keratinocytes and in skin (Hennings et al., 1980; Fuchs, 1990; Tennenbaum et al., 1996a). Further differentiation to the granular layer phenotype is associated with down regulation of both $\beta 1$ and $\beta 4$ integrin expression, loss of adhesion potential to all matrix proteins and is followed by cornified envelope formation and cell death. Differentiating cells ultimately sloughs from the culture dish as mature squames (Yuspa et al., 1989; Tennenbaum et al., 1996b). This program of differentiation in vitro closely follows the maturation pattern of epidermis in vivo.

Wound healing may be induced in vivo by various bioactive agents which directly or indirectly promote growth, differentiation and/or migration of keratinocytes and/or epidermal cells. Thus, U.S. Pat. Nos. 5,591,709 and 5,461,030 describe the use of non-steroidal anabolic hormone such as insulin, growth hormone, triiodothyronine and thyroxine for inducing wound closure. U.S. Pat. No. 5,145,679 describes the use of insulin and pancreatin for inducing wound closure. U.S. Pat. No. 6,541,447 describes the use of a mixture of growth factors and growth hormones for inducing wound closure, and International Application No. PCT/IL01/00675 (WO 02/09639) and corresponding U.S. patent application Ser. No. 09/169,801 describe the use of PKC modulating agents for inducing wound closure. However, there is no teaching in the prior art for utilizing adipocytes, adipocyte or preadipocyte modulators, or molecules secreted by adipocytes, for inducing or accelerating the processes associated with wound healing.

There is thus a widely recognized need for, and it would be highly advantageous to have, new approaches for accelerating the processes associated with wound healing.

SUMMARY OF THE INVENTION

While reducing the present invention to practice, the present inventors uncovered that adipocytes are closely associated with migrating keratinocytes at the skin wound gap during an early stage of the healing process, indicating that adipocytes, adipocyte modulators and adipokines are involved in, and hence influence the healing process of a damaged skin or skin wounds.

It has further been found by the present inventors that the healing process of a damaged skin and skin wounds can be effectively promoted by administering to the skin cells colonizing the damaged skin or skin wound area an adipokine, an adipocyte modulator or a preadipocyte modulator.

Hence, the present invention provides, in one aspect, a method of inducing or accelerating a healing process of a damaged skin or skin wound, the method comprising administering to the skin cells colonizing the damaged skin or skin wound area a therapeutically effective amount of an agent selected from the group consisting of an adipokine, an adipocyte modulator, and a preadipocyte modulator, thereby inducing or accelerating the healing process of the damaged skin or skin wound.

According to another aspect of the present invention, there is provided a method of inducing or accelerating a healing process of a damaged skin or skin wound, the method comprising implanting onto the skin cells colonizing the damaged skin or skin wound area a therapeutically effective amount of adipocytes, preadipocytes or stem cells, thereby inducing or accelerating the healing process of the damaged skin or skin wound.

According to a further aspect of the present invention, there is provided a method of inducing or accelerating a healing process of a damaged skin or skin wound, the method comprising administering to the skin cells colonizing the damaged skin or skin wound area a therapeutically effective amount of a viral vector comprising a polynucleotide coding for an adipokine, thus transforming said skin cells to express and secrete said adipokine, thereby inducing or accelerating the healing process of the damaged skin or skin wound.

According to features in preferred embodiments of the invention described below, the wound is selected from the group consisting of an ulcer, a diabetes related wound, a burn, a sun burn, an aging skin wound, a corneal ulceration wound, an inflammatory gastrointestinal tract disease wound, a bowel inflammatory disease wound, a Crohn's disease wound, an ulcerative colitis, a hemorrhoid, an epidermolysis bulosa wound, a skin blistering wound, a psoriasis wound, seborrheic dermatitis wound, an animal skin wound, a proud flesh wound, an animal diabetic wound, a retinopathy wound, an oral wound (mucositis), a vaginal mucositis wound, a gum disease wound, a laceration, a surgical incision wound and a post surgical adhesions wound.

According to still further features in the described preferred embodiments the ulcer is a diabetic ulcer, a pressure ulcer, a venous ulcer, a gastric ulcer and an HIV related ulcer.

The present invention successfully addresses the shortcomings of the presently known configurations by providing new therapeutics to treat damaged skin or skin wounds.

BRIEF DESCRIPTION OF THE FIGURES

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

The wounds were treated daily with topical application of PBS (control), insulin (10 nM), troglitazone (100 µM), or troglitazone (100 µM)+insulin (10 nM) for six days, then sacrificed, sectioned and analyzed for wound closure. The wound closure was determined by K14 and epidermal differentiation by K1 antibody staining. Wounds were considered positive if the wound was stained positive throughout the entire wound gap. Each bar represents the mean of six replications.

Figure 11:
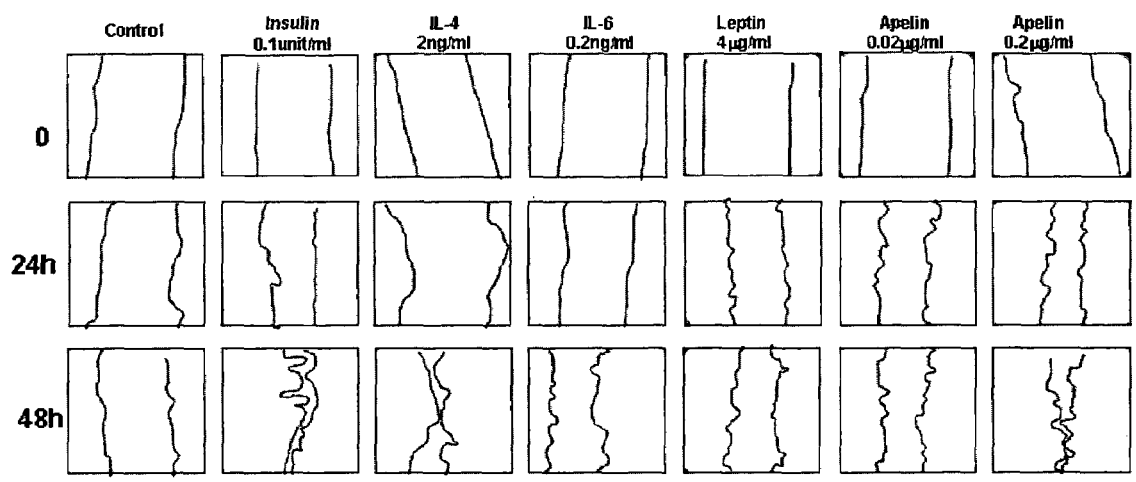

FIG. 11 shows the effect of various adipokines on keratinocytes migration in vitro. Primary keratinocytes were isolated and plated on 5 ml non-coated dishes until confluence in low $Ca^{2+}$ medium, and an artificial crossover scratch was formed in each dish with a 200 µm tip. Cells were either non-treated (control) or treated daily with insulin (0.1 unit/ml equivalent to 1 µM), hIL-4 (2 ng/ml), hIL-6 (0.2 ng/ml), leptin (4 µg/ml) or apelin (0.02 µg/ml and 0.2 µg/ml). Photo documentation was performed utilizing a light microscope at 0, 24 and 48 hrs post treatment. Magnification ×100.

Figure 12:
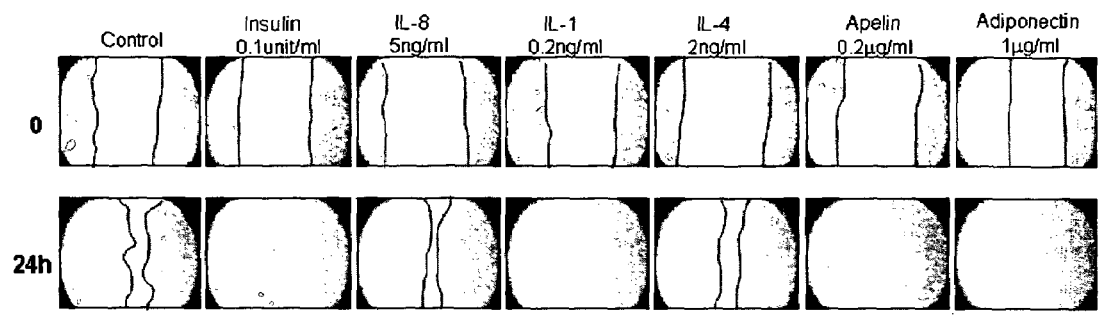

FIG. 12 shows the effect of various adipokines on matrix wound healing in vitro. Primary skin fibroblasts were isolated and plated on 5 ml non-coated dishes until confluence in low $Ca^{2+}$ medium, and an artificial crossover scratch was formed in each dish with a 200 µm tip. Cells were either non-treated (control) or treated with insulin (0.1 unit/ml), hIL-8 (5 ng/ml), hIL-1β (0.2 ng/ml), hIL-4 (2 ng/ml), apelin (0.2 µg/ml) or adiponectin (1 µg/ml), and collected after 24 hrs. Photo documentation was performed utilizing a light microscope at 0 and 24 hrs post treatment. Magnification ×100.

Figure 13:
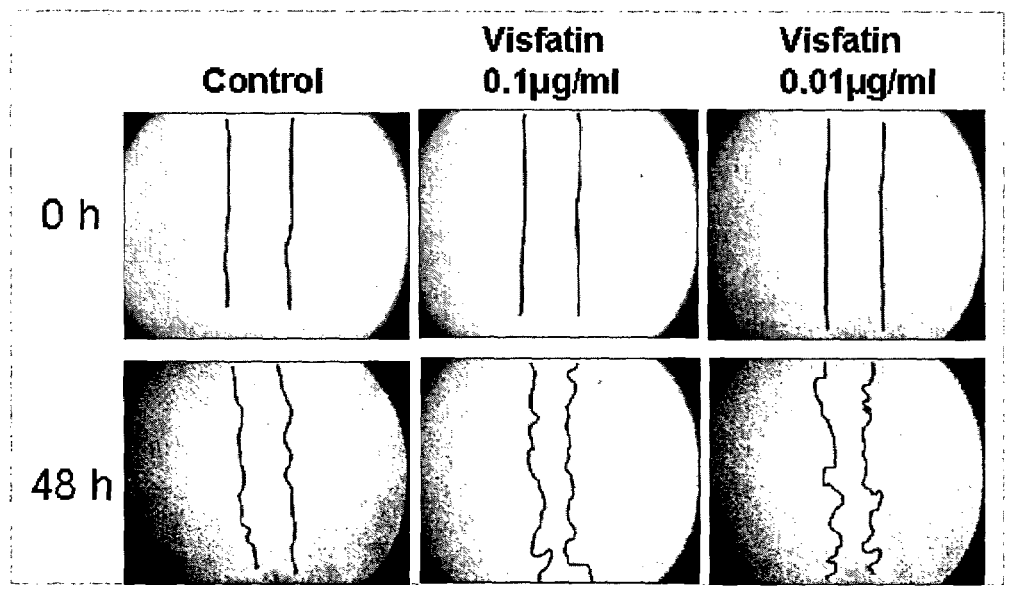

FIG. 13 shows the effect of visfatin on wound healing in vitro. Primary keratinocytes were isolated and plated on 5 ml non-coated dishes until confluence in low $Ca^{2+}$ medium, and an artificial crossover scratch was formed in each dish with a 200 µm tip. Cells were non-treated or treated with visfatin (0.1 ug/ml or 0.01 ug/ml) for up to 48 hrs. Photo documentation was performed utilizing a light microscope at day 0 and 48 hrs post treatment. Magnification ×100.

Figure 14:
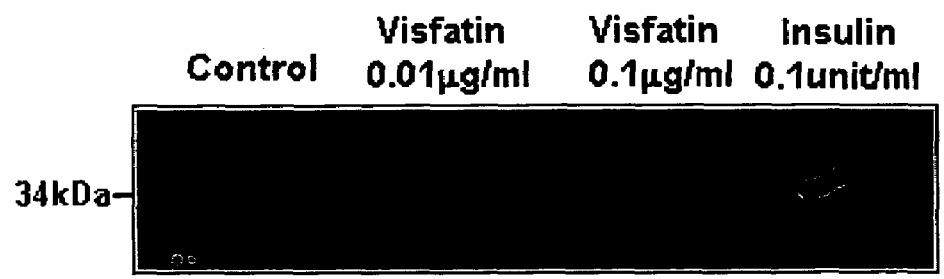

FIG. 14 shows the effect of visfatin on primary keratinocyte proliferation. Primary keratinocytes were isolated and plated on 100 mm tissue dishes and maintained for 5 days in medium with low $Ca^{2+}$ (0.05 mM) until 80% confluence. Next, cells were either non-treated (control) or treated with insulin (0.1 unit/ml 1uM), visfatin (0.01 µg/ml or 0.1 µg/ml). 24 hrs post treatment cells were lyzed and analyzed for PCNA expression by western blot analysis.

Figure 15:
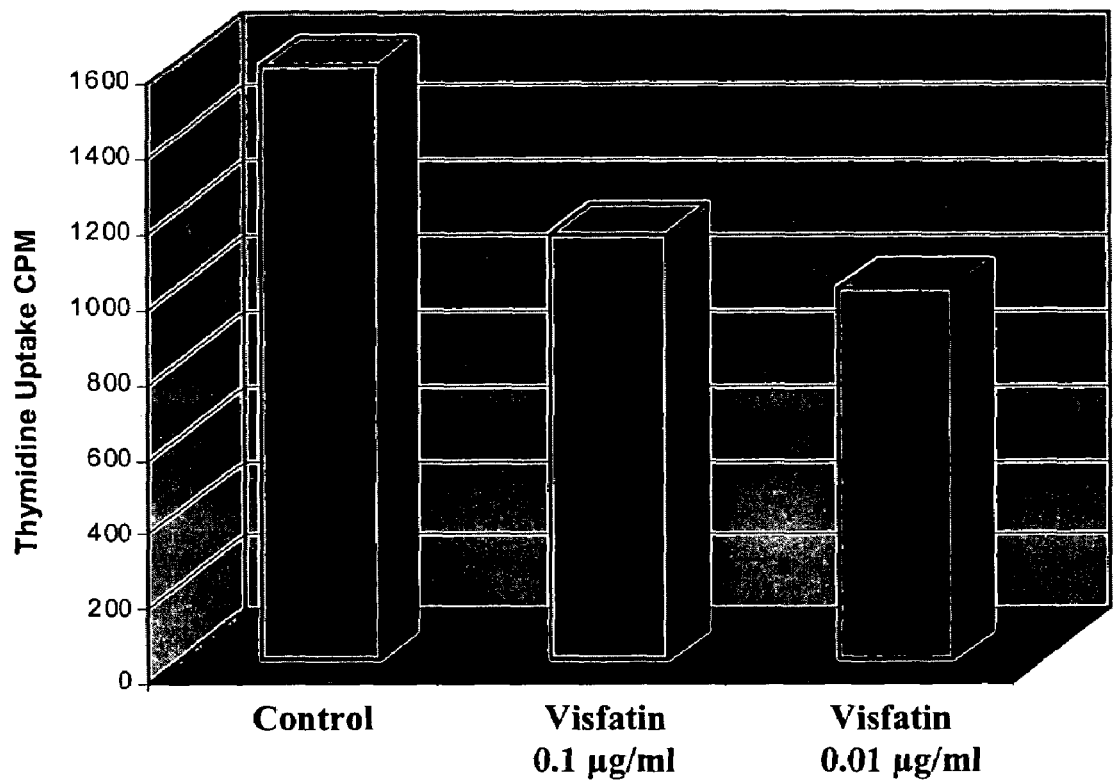

FIG. 15 shows the effect of visfatin on primary keratinocyte proliferation. Primary keratinocytes were isolated, plated on 6 well tissue dishes and maintained for 5 days in medium with low $Ca^{2+}$ (0.05 mM) until 80% confluence. Next, cells were either non-treated or treated with visfatin (0.1 µg/ml or 0.01 µg/ml) for 24 hrs and pulsed with [$^3$H] thymidine (1 uCi/ml) for 1 hour. After incubation, cells were washed 3 times with PBS and 5% TCA was added into each well for 1 hour. The solution was then removed and cells were stabilized in 1M NaOH. The labeled thymidine incorporated into the cells was counted in a $^3$H-window of a Tricarb liquid scintillation counter.

Figure 16:
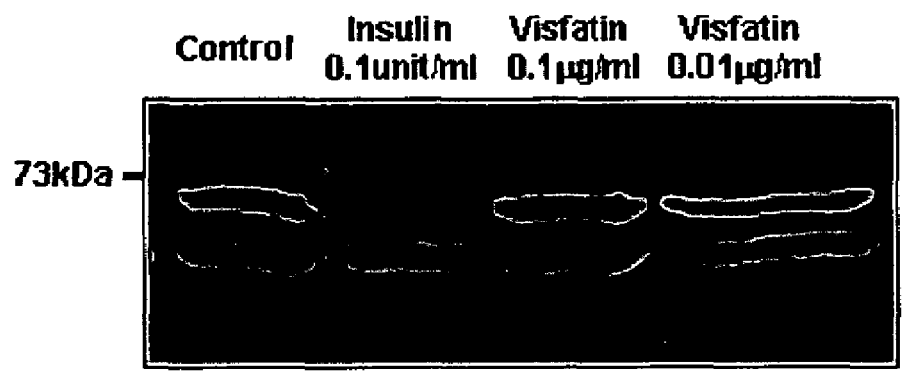

FIG. 16 shows the effect of visfatin on primary keratinocytes differentiation. Primary keratinocytes were isolated, plated on 100 mm tissue dishes and maintained for 5 days in medium with low $Ca^{2+}$ (0.05 mM) until 80% confluence. Next, cells were either non-treated or treated with insulin (0.1 unit/ml 1 µM) or visfatin (0.01 µg/ml or 0.1 µg/ml). 24 hrs post treatment cells were lysed and analyzed for Keratin 1 (K1) expression by western blot analysis.

Figure 17:
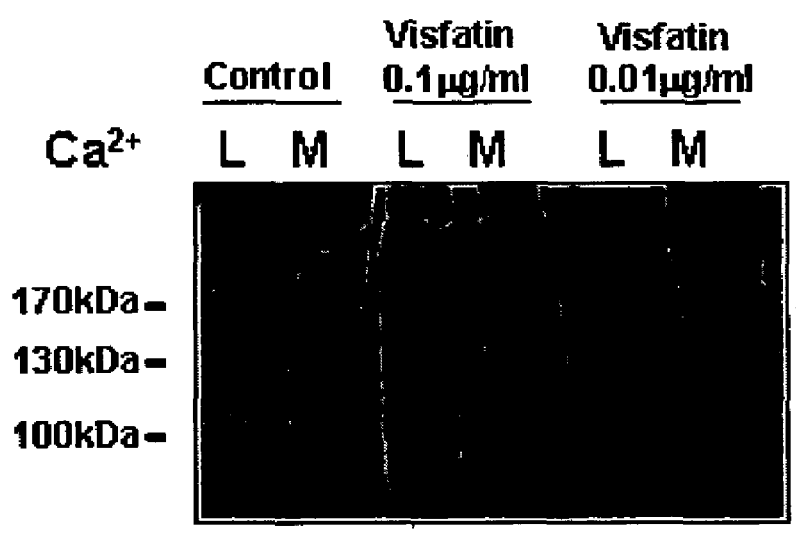

FIG. 17 shows the effect of visfatin on primary keratinocytes differentiation. Primary keratinocytes were isolated, plated on 100 mm tissue dishes and maintained for 5 days in medium with low $Ca^{2+}$ (0.05 mM) until reaching 80% confluence. Next, cells were either non-treated or treated with visfatin (0.01 µg/ml or 0.1 µg/ml). Terminal differentiation was induced by adding $Ca^{2+}$ to the medium 6 hrs post treatment. M=0.12 mM, L=no added calcium. 24 hours post treatment cells were lysed and analyzed for filaggrin expression by western blot analysis.

Figure 18:
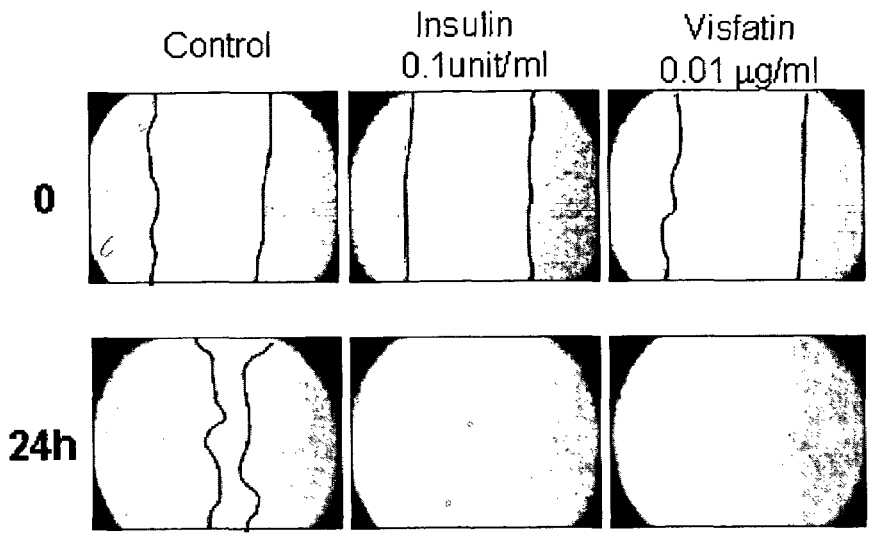

FIG. 18 shows the effects of visfatin on matrix wound healing in vitro. Primary fibroblasts were isolated and plated on 5 ml non-coated dishes until confluence in low $Ca^{2+}$ medium, and an artificial crossover scratch was formed in each dish with a 200 µm tip. Cells were either non-treated or treated with either visfatin (0.01 µg/ml) or insulin (0.1 unit/ml); and collected after 24 hrs. Photo documentation was performed utilizing a light microscope at day 0 and 24 hrs post treatment. Magnification ×100.

Figure 19:
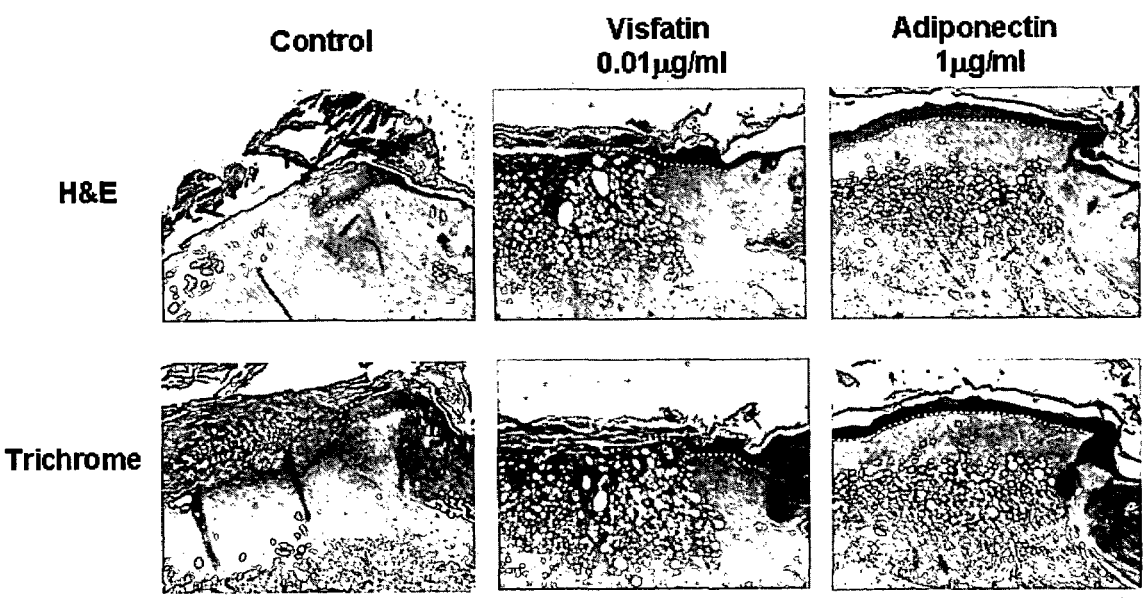

FIG. 19 shows the effect of adipokines on wound healing in vivo. Slide sections represent the widest area of the wound, subjected to H&E (upper panel) and Masson Trichrome (lower panel) histochemical staining. Epidermis is stained deep-purple (H&E) or red (Trichrome) and underlined by yellow dotted line. Dermis is stained pink in the H&E panel and stained blue in the Trichrome panel due to major presence of collagen fibers.

Figure 20:
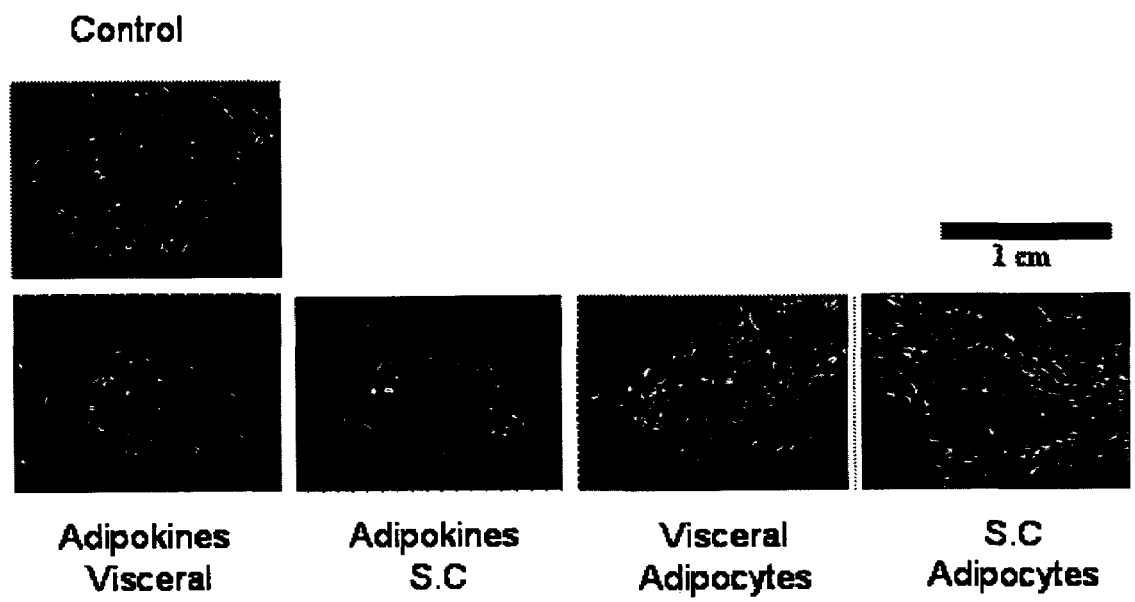

FIG. 20 shows the effect of adipocytes and adipokines on wound healing. Full thickness wounds were performed on 8-10 week old C57BL mice. Wounds were treated daily, for 5 days, with either PBS (control), adipokines collected from the secretion of visceral human primary preadipocytes, adipokines collected from the secretion of subcutaneous (S.C) human primary preadipocytes, homogenized cell extract from human subcutaneous layer or homogenized cell extract from human liposuction. Morphological assessment was performed daily utilizing photo documentation. Pictures represent average wound size in mice from each treatment group 5 days post wounding.

Figure 21:
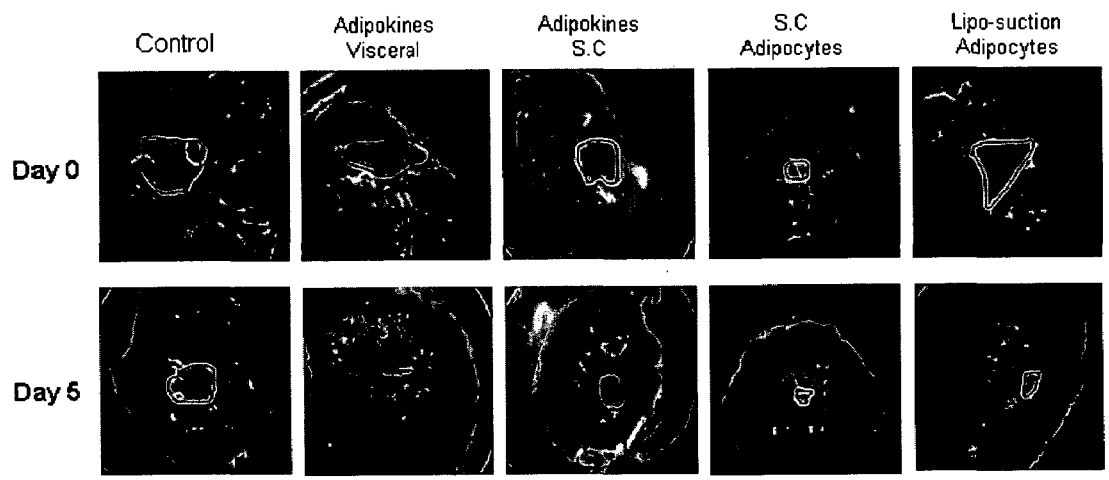

FIG. 21 shows the effect of adipocytes and adipokines on human skin wound healing in the CAM ex-vivo model system. Skin biopsies were obtained from human abdomen with the underlying hypodermis layer. The skin was sectioned into circular pieces of 1.5 cm diameter×1 cm explants and grafted on 8-9 old fertilized eggs. Wounds were performed utilizing a 6 mm punch prior to grafting. Wounds were treated daily, for 5 days, with 20 µl of either PBS (control), adipokines collected from the secretion of visceral human primary preadipocytes, adipokines collected from the secretion of subcutaneous (S.C) human primary preadipocytes, homogenized autologous cell extract from subcutaneous layer or homogenized autologous cell extract from liposuction. Pictures represent experiments of full thickness (control and adipokines treatments) or partial thickness (adipocyte homogenates). Morphological assessment was performed daily utilizing photo documentation under binocular microscope—actual size.

DESCRIPTION OF THE PREFERRED EMBODIMENTS

The present invention is of methods and pharmaceutical compositions for inducing or accelerating the healing process of a damaged skin or skin wounds. More particularly, the present invention utilizes bioactive molecules secreted by adipocytes (adipokines), adipocytes and preadipocytes attractants, adipocytes and preadipocyte modulators, as well as adipocytes and cells capable of differentiating into adipocytes such as preadipocytes and stem cells, for accelerating the healing process of a damaged skin or skin wounds.

Before explaining at least one embodiment of the invention in detail, it is to be understood that the invention is not limited in its application to the details of construction and the arrangement of the components set forth in the following description or exemplified in the Examples section. The invention is capable of other embodiments or of being practiced or carried out in various ways. Also, it is to be understood that the phraseology and terminology employed herein is for the purpose of description and should not be regarded as limiting.

Adult skin consists of several layers including: a keratinized stratified epidermis, an underlying thick layer of collagen-rich dermal connective tissue providing support and nourishment, and a subcutaneous adipose tissue. Skin serves as the protective barrier against the outside world. Therefore, any injury or break in the skin must be rapidly and efficiently mended. As described in the Background section hereinabove, the first stage of skin repair is achieved by formation of the clot that plugs the initial wound. Thereafter, inflammatory cells, fibroblasts and capillaries invade the wound bed to form a granulation tissue. The following stages involve re-epithelization of the wound, where basal keratinocytes have to lose their hemidesmosomal contacts and migrate into the granulation tissue to cover the wound. Following keratinocyte migration, keratinocytes enter a proliferative boost, which allows replacement of cells lost during wound formation. After the wound is covered by a monolayer of keratinocytes (i.e., epidermal closure) new stratified epidermis is formed and the new basement membrane is reestablished (Weinstein, 1998; Singer and Clark, 1999; Whitby and Ferguson, 1991; Kiritsy et al., 1993).

While conducting experiments in wound healing research, the inventors of the present invention unexpectedly uncovered that adipocytes are closely associated with migrating keratinocytes at the wound area, during an early stage of the wound healing process. Accordingly, Example 1 hereinbelow illustrates that the appearance of migrating keratinocytes at the wound gap was directly correlated with appearance of recruited adipocytes at the same area. Moreover, insulin treated wounds recruited more adipocytes to the wound gap, and subsequently healed faster, than control, untreated wounds. This newly uncovered close association of adipocytes and migrating keratinocytes at healing wounds, coupled with the direct correlation observed between recruited adipocytes incidence and wound healing efficiency, indicate that adipocytes, adipocyte modulators and adipocyte products (adipokines) are involved in, and hence may be used to influence, the wound healing process.

Adipocytes secrete a number of bioactive molecules, known as adipokines, which play a role in the maintenance of energy homeostasis by regulating insulin secretion, insulin action, glucose and lipid metabolism, energy balance, inflammation, and reproduction.

However, the possible involvement of adipocytes-secreted bioactive molecules in wound healing has not been taught nor suggested by the prior art.

Based on the initial findings described above, and while further reducing the present invention to practice, the inventors of the present invention anticipated and thereafter uncovered that an exemplary adipokine, adipsin, which was chosen out of the list of known adipokines, substantially accelerated keratinocytes migration in vitro and effectively promoted healing of skin wounds in vivo (see Example 3 herein). Further experiments uncovered that other adipokines such as adipsin, apelin and IL-4, also substantially accelerated keratinocytes migration in vitro, while positive albeit less significant effects were obtained with the adipokines IL-6, leptin and visfatin, as illustrated in Examples 3, 4 and 6 hereinafter. In addition, IL-1, apelin, adiponectin, visfatin and to a lesser extent also IL-8, promoted fibroblast migration in vitro, as illustrated in Examples 5 and 6 hereinafter.

Furthermore, both adipsin and adiponectin, found to substantially enhance both keratinocytes and fibroblast migration, were further found to significantly promote wound healing in vivo, as illustrated in Examples 3 and 7 hereinafter. Visfatin, that was found to enhance keratinocytes migration in vitro, was further found to attract adipocytes to the wound side and to reduce inflammation in vivo, indicating that it may be beneficial in late wound healing stages (see Example 7 hereinafter).

The inventors of the present invention further uncovered that adipocytes and preadipocytes derived factors, as well as homogenate of adipocytes or preadipocytes from the subcutaneous or visceral origins, promoted wound closure in vivo, as illustrated in Example 8 hereinafter. These results were further supported by experiments with human skin wounds utilizing the chick chorioallantioic membrane (CAM) ex vivo model system, which provides a unique experimental design for testing the efficacy of selected agents on human wounds. As illustrated in Example 9 hereinafter, efficient wound healing was observed in human wounds treated with adipokines extracted from preadipocytes and/or autologous cell homogenates, exemplifying the importance of adipocytes and adipocytes derived factors in the promotion of wound healing.

Thus, according to one aspect of the present invention there is provided a method of inducing or accelerating a healing process of a damaged skin or skin wound, comprising administering to the skin cells colonizing the damaged skin or skin wound area a therapeutically effective amount of an agent selected from the group consisting of an adipokine, an adipocyte or preadipocyte modulator, thereby inducing or accelerating the healing process of the damaged skin or skin wound.

To facilitate understanding of the invention set forth in the disclosure that follows, a number of terms are defined herein.

The term "wound" used herein refers broadly to injuries to the skin and subcutaneous tissue initiated in any one of a variety of ways (e.g., pressure sores from extended bed rest, wounds induced by trauma, cuts, ulcers, burns and the like) and with varying characteristics. Wounds are typically classified into one of four grades depending on the depth of the wound: (i) Grade I: wounds limited to the epithelium; (ii) Grade II: wounds extending into the dermis; (iii) Grade III: wounds extending into the subcutaneous tissue; and (iv) Grade IV (or full-thickness wounds): wounds wherein bones are exposed (e.g., a bony pressure point such as the greater trochanter or the sacrum).

The term "partial thickness wound" used herein refers to wounds that encompass Grades I-III; examples of partial thickness wounds include burn wounds, pressure sores, venous stasis ulcers, and diabetic ulcers.

The term "deep wound" used herein is meant to include both Grade III and Grade IV wounds.

The term "chronic wound" used herein refers to a wound that exhibits impaired healing parameters interfering with the physiological sequence of events. These wounds tend to prolong and/or halt healing time course, subjecting the wounds to further complications such as recurrent infections and necrosis.

The term "skin wound" as used herein refers to any type of epithelial wound including, but not limited to, an ulcer such as a diabetic ulcer, a pressure ulcer, a venous ulcer, a gastric ulcer and an HIV-related ulcer, a diabetes-related wound, a burn, a sun burn, an aging skin wound, a corneal ulceration wound, an inflammatory gastrointestinal tract disease wound, a bowel inflammatory disease wound, a Crohn's disease wound, an ulcerative colitis, a hemorrhoid, an epidermolysis bulosa wound, a skin blistering wound, a psoriasis wound, an animal skin wound, a proud flesh wound, an animal diabetic wound, a retinopathy wound, an oral wound (mucositis), a vaginal mucositis wound, a gum disease wound, a laceration, a surgical incision wound and a post surgical adhesions wound.

The term "skin damage" as used herein refers to any type of skin damage or condition such as, for example, wrinkles (e.g., ultraviolet irradiation-induced wrinkles), skin lines, crevices, bumps, large pores (e.g., associated with adnexal structures such as sweat gland ducts, sebaceous glands, or hair follicles), or unevenness or roughness, loss of skin elasticity (loss and/or inactivation of functional skin elastin), sagging (including puffiness in the eye area and jowls), loss of skin firmness, loss of skin tightness, loss of skin recoil from deformation, discoloration (including undereye circles), blotching, sallowness, hyperpigmented skin regions such as age spots and freckles, keratoses, abnormal differentiation, hyperkeratinization, elastosis, collagen breakdown, and other histological changes in the stratum corneum, dermis, epidermis, the skin vascular system (e.g., telangiectasia or spider vessels), and underlying tissues, especially those proximate to the skin.

The present invention contemplates treating all wound types and of all grades, including deep wounds and chronic wounds, as well as skin damage.

The term "healing" in respect to a wound or a skin damage refers to a process to repair a wound, or to repair the skin damage.

The phrase "inducing or accelerating a healing process of a skin wound or skin damage" refers to either the induction of the formation of granulation tissue of wound contraction and/or the induction of repithelialization (i.e., the generation of new cells in the epithelium). Wound healing is conveniently measured by decreasing wound area.

The term "adipokine" as used herein refers to any bioactive molecule which is secreted by adipocytes in vivo or in vitro, including, but not limited to, adipocyte-secreted enzymes, growth factors, cytokines and hormones. Preferably, the adipokine of the present invention is selected from the group consisting of complement factors D (adipsin), C3 and B, adiponectin (Acrp30), apelin, visfatin, resistin, leptin, lipoprotein lipase (LPL), plasminogen activator inhibitor-1 (PAI-1), tumor neorosis factor α (TNF-α), IL-1β, IL-4, IL-6, IL-8, angiotensin I-IV (angiotensin IV is an active angiotensin II fragment) and cycloanalogues thereof, angiotensinogen, 1-butyrylglycerol(monobutyrin), matrix metalloproteinases 2, matrix metalloproteinases 9 and vascular endothelial growth factor (VEGF). Preferably the adipokine is adipsin or adiponectin.

As has been found in accordance with the present invention, the healing process of a damaged skin or skin wounds may also be induced or accelerated by administering to the skin cells colonizing the damaged skin or skin wound an adipocyte modulator.

The phrase "adipocyte modulator" as used herein refers to any molecule capable of modulating expression and/or secretion of an adipokine from adipocytes, as well as to any molecule capable of modulating adipocytes differentiation; enhancing adipocytes proliferation; promoting adipocytes migration; or attracting adipocytes to the wound gap.

Adipocytes are differentiated from preadipocytes in a process known as adipogenesis. In culture, adipogenesis is fully dependent on insulin, dexamethasone and isobuthylmethylxanthine, stressing the involvement of insulin, glucocorticoid and cAMP pathways.

While many signaling and biochemical pathways play an imperative role in this process, most of the known changes that occur during adipogenesis are at the gene transcription level. The key transcriptional factors involved in the adipogenic process include proteins belonging to the CCAAT/enhancer binding protein family, adipocyte determination and differentiation dependent factor 1 (also known as sterol regulatory element-binding protein 1), and peroxisome proliferator-activated receptor (PPAR)-γ (Rangwala and Lazar, 2000).

The peroxisome proliferator-activated receptors (PPARs) comprise three types: PPARα, PPARβ and PPARγ. They are ligand-inducible nuclear receptors that directly modulate gene activity by binding to defined nucleotide sequences in the promoter region of target genes. PPARγ plays a crucial role in the terminal differentiation by transactivation of adipocyte-specific genes. Recent results suggest a cross talk between PPARs and the cholesterol metabolism pathway in the epidermis. All PPAR isoforms are expressed in embryonic and mature skin. PPARγ expression dramatically increases at the late stages of fetal maturation. In postnatals, as well as in adult skin, the expression of PPARγ is decreased. An important role has been suggested for PPARβ and PPARα in keratinocyte differentiation during epidermis formation (Wabli, 2002). It has been also demonstrated that PPARβ and PPARα are up-regulated at the edges of wounded skin and that null mice of these isoformes are wound healing impaired (Michalnik et al., 2001). Yet, the involvement of PPARγ in the wound healing process has not been described nor suggested in the prior art.

U.S. Pat. No. 6,403,656 describes the use of PPARγ activators for treating skin disorders related to an anomaly of the differentiation of epidermic cells. In addition, International Application No. PCT/US99/28101 describes the use of PPARγ activators, such as a prostaglandin J2 or D2, for treating obesity and diabetes. However, none of these disclosures teaches or suggests using PPARγ activators, or inhibitors, for use in healing wounds.

While further reducing the present invention to practice, the inventors of the present invention uncovered that PPARγ activity is inversely related to the wound healing process. Accordingly, Example 2 hereinafter illustrates that administering troglitazone, a PPARγ agonist, inhibited wound contraction. On the other hand, administering GW9662 (2-chloro-5-nitrobenzanilide), which is a PPARγ antagonist, promoted wound contraction.

Thus, according to another aspect of the present invention there is provided a method of inducing or accelerating a healing process of a skin wound, comprising administering to the skin wound a therapeutically effective amount of an agent capable of modulating differentiation of adipocytes, thereby inducing or accelerating the healing process of the skin wound. The agent according to this aspect of the present invention may be any agonist or antagonist of any factor, such as a transcriptional factor which is involved in adipocytes differentiation, including, but not limited to, a protein belonging to the CCAAT/enhancer binding protein family, adipocyte determination and differentiation dependent factor 1, and PPARγ. Preferably, the agent is a PPAR-γ antagonist, more preferably GW9662.

In addition to adipocytes differentiation modulators, the wound healing process may be promoted by utilizing other adipocyte modulators. Thus, according to the teaching of the present invention, a healing process of a skin wound can be induced or accelerated by administering to the skin wound a therapeutically effective amount of an agent which is capable of: (i) modulating expression and/or secretion of an adipokine from adipocytes, (ii) enhancing adipocytes proliferation, (iii) enhancing adipocytes migration, or (iv) attracting adipocytes to the wound or damaged skin area.

An assay readily exercisable by one ordinarily skilled in the relevant art of determining whether a specific agent, e.g., an adipokine or pre/adipocyte modulator, is indeed an inducer or accelerator of a wound healing process, is offered in context of the present invention.

Thus, the capacity of an adipokine or a pre/adipocyte modulator to induce or accelerate a healing process of a skin wound can be determined by administering the adipokine or pre/adipocyte modulator in question to skin cells colonizing the damaged skin or skin wound area wound and evaluating the treated damaged skin or wounds for keratinocytes migration and/or epidermal closure and/or wound contraction.

Preferably, the skin wound is effected on the backs of a C57BL mouse by incision and treated with one or more applications, each with one or more concentrations of the adipokine or pre/adipocyte modulator.

At a desired time period post wounding, preferably of about 6-7 days, the mouse is sacrificed and wound biopsies are sampled. The wound biopsies are then analyzed for keratinocytes migration across the wound gap and/or for epidermal closure of the wound gap and/or wound contraction, using methods known in the art, but preferably using the procedures described in the Examples section hereinafter.

A significant increase in the incidence of keratinocytes migration and/or epidermal closure and/or wound contraction, over an untreated control, would determine that a tested adipokine or adipocyte modulator is capable of inducing or accelerating a healing process of a damaged skin or skin wound.

According to another aspect of the present invention, adipocytes, preferably human, more preferably human autologous adipocytes, are implanted onto the skin cells colonizing the damaged skin or skin wound, so as to induce or accelerate the healing process of the damaged skin or skin wound.

Adipocytes may be obtained from an adipose tissue of any animal source, preferably from a human donor, most preferably from an autologous human source. The adipose tissue may be sampled from a subcutaneous or perirenal site, preferably subcutaneous, using well recognized protocols such as surgical, suction, liposuction, panniculectomy, or via biopsy. The adipocyte cells are preferably separated from the adipose tissue sample by using enzymes which destroy physical cell contacts (e.g., collagenases), or by using mechanical agitation, sonic or ultrasonic energy and the like. The separated adipocytes can be cultured using suitable tissue culture techniques known in the art such as, for example, described in details in International Application No. PCT/US00/30623. The cultured adipocytes are allowed to grow until near-confluence is reached, then removed by gentle scrapping from the growth medium and implanted onto the wound.

Adipocytes can also be generated from cultured preadipocytes. The term "preadipocyte" as used herein refers to any cell which is capable of differentiating into an adipocyte. Preferably, preadipocytes are human preadipocytes, more preferably autologous preadipocytes isolated from the patient's own adipose or other tissue. The adipose tissue may be sampled from subcutaneous or perirenal sites using well recognized protocols such as surgical, suction liposuction, panniculectomy, or via biopsy. The preadipocyte cells may be isolated from the sampled tissue by using methods such as described by Rodbell and Krishna (1974). Isolated preadipocytes can be grown, expanded and differentiated into adipocytes in vitro, using methods and procedures such are described by Hauner et al. (1989), Digby et al. (1998), and in International Application No. PCT/US00/02208. The differentiated adipocytes can be harvested from the culture medium using harvesting methods such as described by Freshney (1994) and implanted onto the wound preferably via a grafting chamber such as described in International Application No. PCT/US97/0061. The grafting chamber can be removed from the wound after at least 1 day, preferably after at least 1 week subsequent to the implantation of the adipocytes. Optionally, prior to their implantation, the adipocytes are exposed to an adipocyte modulator, such as, without limitation, a PPAR-γ antagonist, preferably GW9662.

Thus, according to another aspect of the present invention, preadipocytes are implanted onto the skin cells colonizing the damaged skin or skin wound, so as to induce or accelerate the healing process of the damaged skin or skin wound.

The preadipocytes can be isolated, grown and expanded in vitro, using the methods and procedures such as described for adipocytes hereinabove, but omitting the differentiation step. The non-differentiated preadipocytes are harvested from the culture medium and implanted onto the wound using procedures such as described for adipocytes hereinabove. Optionally, prior to their implantation, the preadipocytes are exposed to a preadipocyte modulator, such as, without limitation, a PPAR-γ antagonist, preferably GW9662.

The term "preadipocytes modulator" as used herein refers to any molecule capable of enhancing differentiation of preadipocytes to adipocytes by adipogenesis as described hereinabove. Preadipocyte modulators may be, without limitation, major transcriptional regulators such as adipocyte determination and differentiation factor-1 (ADD1)/sterol regulatory element binding protein 1 (SREBP-1), members of the CCAAT/enhancer binding proteins (C/EBPs) and a PPAR-γ antagonist, preferably GW9662.

Adipocytes and/or preadipocytes can also be generated from cultured stem cells. The phrase "stem cells" as used herein refers to embryonic or adult cells which are not terminally differentiated, which can divide without limit, and divides to yield cells that are either stem cells or which irreversibly differentiate to yield a new type of cell such as a preadipocyte or an adipocyte.

Isolation and ex vivo expansion of stem cells can be performed using methods well known in the art. For example, Van Epps et al. (1994) and Emerson (1996) describe procedures for isolation and human hematopoietic stem cells from bone marrow, peripheral blood or a neonatal umbilical cord blood, and their expansion in culture. Human embryonic stem cells (hESC) can be prepared from human blastocyst cells, obtained from human in vivo preimplantation embryos, or in vitro fertilized embryos, using methods such as described in U.S. Pat. No. 5,843,780 and by Reubinoff et al. (2000). Human mesenchymal stem cells (hMSC) can be isolated and expanded using methods such as described in U.S. Pat. Nos. 5,197,985, 5,486,359 and 6,214,369. The hMSC are found in bone marrow, blood, dermis and periosteum which are capable of differentiating into any of the specific types of mesenchymal tissues, such as an adipose tissue.

According to a further aspect of the present invention, stem cells can be implanted directly onto the skin cells colonizing the damaged skin or skin wound and allowed for differentiation into adipocytes in vivo, with or without the co-administration of factors facilitating such differentiation. Alternatively, the stem cells. can be differentiated into preadipocytes or adipocytes ex vivo and then implanted onto the damaged skin or skin wound.

Cultured hMSC can be induced for adipogenic differentiation, using methods such as described in U.S. Pat. No. 6,322,784. Accordingly, adipocytes can be generated from primary hMSC by exposing the stem cells to a glucocorticoid and a compound capable of upregulating cAMP production, such as a phosphodiesterase inhibitor, or by inhibiting degradation of cAMP. The adipocytes or preadipocytes generated from stem cells are subsequently harvested and implanted onto wounds using procedures such as described above, so as to induce or accelerate the healing process of the damaged skin or skin wounds.

In an alternative embodiment of the present invention, skin cells colonizing the damaged skin or skin wound area are transformed to express and secrete an adipokine, thereby inducing or accelerating the healing process of the damaged skin or skin wound.

The skin cells colonizing the damaged skin or skin wound may be of any cell type which is involved in the wound healing process, such as keratinocytes, fibroblasts, adipocytes or preadipocytes. The cells can be transformed by a polynucleotide encoding an adipokine as defined hereinbefore. Alternatively, the cells can be transformed by a polynucleotide encoding a polypeptide capable of an adipokine activity, such as the polynucleotide encoding adipsin/complement D activity described in U.S. Pat. No. 5,223,425.

The suitable polynucleotide can be introduced into cells by any one of a variety of known methods within the art. Such methods are generally described in Sambrook et al., (1989, 1992), Ausubel et al., (1989), Chang et al., (1995), Vega et al., (1995), Rodriguez and Denhardt (1988) and Gilboa et al., (1986), and include, for example, stable or transient transfection, lipofection, electroporation and infection with recombinant viral vectors. U.S. Pat. No. 4,866,042 discloses a list of vectors involving the central nervous system, and U.S. Pat. Nos. 5,464,764 and 5,487,992 describe positive-negative selection methods for inducing homologous recombination.

A preferred approach for introducing a polynucleotide encoding an adipokine into wound cells is by using a viral vector. Viral vectors offer several advantages including higher efficiency of transformation, and targeting to, and propagation in, specific cell types. Viral vectors can also be modified with specific receptors or ligands to alter target specificity through specific cell receptors, such as cancer cell receptors.

Retroviral vectors represent one class of vectors suitable for use with the present invention. Defective retroviruses are routinely used in transfer of genes into mammalian cells (Miller, 1990). A recombinant retrovirus including an adipokine encoding polynucleotide can be constructed using well-known molecular techniques. Portions of the retroviral genome can be removed to render the retrovirus replication defective and the replication defective retrovirus can then be packaged into virions, which can be used to infect target cells through the use of a helper virus and while employing standard techniques. Protocols for producing recombinant retroviruses and for infecting cells in vitro or in vivo with such viruses can be found, for example, in Ausubul et al., (1989). Retroviruses have been used to introduce a variety of genes into many different cell types, including epithelial cells endothelial cells, lymphocytes, myoblasts, hepatocytes and bone marrow cells.

Another suitable expression vector may be an adenovirus vector. The adenovirus is an extensively studied and routinely used gene transfer vector. Key advantages of an adenovirus vector include relatively high transduction efficiency of dividing and quiescent cells, natural tropism to a wide range of epithelial tissues and easy production of high titers (Russel, 2000). The adenovirus DNA is transported to the nucleus, but does not integrate thereinto. Thus the risk of mutagenesis with adenoviral vectors is minimized, while short term expression is particularly suitable for treating cancer cells, such as multidrug resistant cancer cells. Adenoviral vectors used in experimental cancer treatments are described by Seth et al., (1999).

Features that limit expression to particular cell types can also be included. Such features include, for example, promoter and regulatory elements that are specific for the desired cell type. The viral vector may also include a nucleotide sequence encoding a signal for secretion of the antibody fragment to the outside of the cell. Secretion signals generally contain a short sequence (7-20 residues) of hydrophobic amino acids. Secretion signals suitable for use in the present invention are widely available and are well known in the art (see, for example, Von Heijne, 1985, and Lej et al., 1987).

The recombinant vector can be administered in several ways. If viral vectors are used, the procedure can take advantage of their target specificity and consequently, such vectors do not have to be administered locally. However, local administration, for example, subcutaneous injection to the proximal wound area, can provide a quicker and more effective treatment. Following injection, the viral vectors will circulate until they recognize host cells with appropriate target specificity for infection.

According to one aspect of the present invention, an adipokine or an adipocyte modulator can be used in therapy per se or as an active ingredient of a pharmaceutical composition adapted for topical or subcutaneous application.

According to another aspect of the present invention, adipocyte, preadipocytes or stem cells can be used in therapy per se or as an active ingredient of a pharmaceutical composition adapted for implantation onto skin cells.

According to a further aspect of the present invention, viral vector comprising a polynucleotide coding for an adipokine can be used in therapy per se or as an active ingredient of a pharmaceutical composition adapted for local, particularly subcutaneous, administration.

As used herein, the phrase "pharmaceutical composition" refers to a preparation of one or more of the active ingredients described herein with other chemical components such as physiologically suitable carriers and excipients. The purpose of a pharmaceutical composition is to facilitate administration of a compound to an organism.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of an administered active ingredient. An adjuvant is included under these phrases.

The term "excipient" as used herein refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Pharmaceutical compositions of the present invention may be manufactured by processes well known in the art, e.g., by means of conventional mixing, dissolving, granulating, dragee-making, levigating, emulsifying, encapsulating, entrapping and/or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which can be used pharmaceutically.

According to the present invention, the pharmaceutically acceptable carrier is suitable for topical application and can be, for example, but is not limited to, a gel, a cream, a paste, a lotion, a spray, a suspension, a powder, a dispersion, a salve and an ointment, as is further detailed hereinunder. Solid supports can also be used for prolonged release of the active ingredient into the wound.

Pharmaceutical compositions suitable for use in context of the present invention include compositions wherein the active ingredients are contained in an amount effective to achieve the intended purpose. More specifically, a therapeutically effective amount means an amount of active ingredients effective to induce or accelerate wound healing.

Determination of a therapeutically effective amount is well within the capability of those skilled in the art, especially in light of the detailed disclosure provided herein, the assay disclosed herein and the Examples section that follows.

For any preparation used in the methods of the invention, the therapeutically effective amount or dose can be estimated initially from a skin wound assay using experimental animals, as well as ex vivo implantation of human skin on the CAM as described hereinabove. Such information can be used to more accurately determine useful doses in humans.

Toxicity and therapeutic efficacy of the active ingredients described herein can be determined by standard pharmaceutical procedures in vitro, in cell cultures, ex vivo, skin implants on the CAM or experimental animals. The data obtained from these in vitro and cell culture assays, ex vivo and animal studies can be used in formulating a range of dosage for use in human. The dosage may vary depending upon the dosage form employed and the route of administration utilized. The exact formulation, route of administration and dosage can be chosen by the individual physician in view of the patient's condition (See, e.g., Fingl, et al., 1975).

Dosage amount and interval may be adjusted individually to levels of the active ingredient which are sufficient to, for example, induce wound healing (minimal effective concentration, MEC). The MEC will vary for each preparation, but can be estimated from in vitro data. Dosages necessary to achieve the MEC will depend on individual characteristics and route of administration.

Depending on the severity and responsiveness of the wound to be treated, dosing can be of a single or a plurality of administrations, with course of treatment lasting from several days to several weeks or until diminution of wound is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredients. The pack may, for example, comprise metal or plastic foil formed into a tube for dispensing formulations for topical administration. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

It will be appreciated that the preferred mode of administration of the active ingredients of the present invention is topical—local administration, yet systemic administration, via acceptable administration routes, such as oral, intramuscular, intravenous, subcutaneous, transdermal, peritoneal, and the like using suitable formulations, as is well known in the art are not excluded.

Thus, the present invention provides novel methods and compositions for use in treatment of wounds by utilizing adipocytes, cells which can differentiate into adipocytes, adipocyte modulators and molecules secreted by adipocytes, for inducing or accelerating healing of wounds safely and effectively.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples. All the US patents and other publications cited in the specification are herein incorporated by reference in their entirety as if fully disclosed herein.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A Laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods (i) Materials.

All standard chemicals were from (Sigma-Aldrich, St. Louis, USA). Paraplast Embedding Medium was also purchased from Sigma. Anti keratin 14 antibody and anti keratin 1 polyclonal antibody were purchase from Bacto-Covance (Richmond, Calif. USA). Biotinylated goat anti-rabbit antibody and streptavidin-horseradish peroxidase (HRP) were purchased from ZYMED Laboratories Inc. (San Francisco, Calif. USA). GW9662 was purchased from Cayman Chemicals (Ann Arbor Mich. USA). Adipsin (complementing factor D) was purchased from Calibiochem (San Diego Calif. USA). Hematoxylin was purchased from DAKO corp. (Carpinteria Calif. USA) eosin was purchased from ICN Biomedicals Inc. (Aurora Ohio USA) and entellan was purchased from MERCK (Darmstadt Germany).

(ii) Isolation and Culture of Murine Keratinocytes.

Primary keratinocytes were isolated from newborn skin as described in reference 18. Keratinocytes were cultured in Eagle's Minimal Essential Medium (EMEM) containing 8% Chelex (Chelex-100, BioRad) treated fetal bovine serum. To maintain a proliferative basal cell phenotype, the final $Ca^{2+}$ concentration was adjusted to 0.05 mM. Experiments were performed five to seven days after plating.

(iii) Keratinocytes Migration Assay.

Primary mouse keratinocytes were untreated or treated with, PPARγ antagonist GW9662 (µM) or PPARγ agonist troglitazone (µM). Wound Scratch Assay was performed 24 hours following treatment, and representative fields were photographed immediately after the wounding (Day 0) and 48 ours later (Day 2). The average of wound closure represented as percentage in comparison to the initial width of the wound scratch (% of wound closure).

(iv) Wound Healing Assay.

Full thickness wounds were effected on backs of C57BL mice by 20 mm incision and were treated daily, for 6 days, with various agents. The mice were sacrificed six days after wounding. Wound biopsies were sampled, processed and analyzed morphologically and/or histochemically and/or immunohistochemically for various wound healing parameters, i.e., wound contraction, adipocytes migration and differentiation, epidermal migration, and epidermal closure.

(v) Wound Contraction Analysis.

The wound area was measured and compared to untreated control wounds; and wound contraction was calculated as the percent reduction of the wound area.

(vi) Preparation of Paraffin Embedded Wound Sections.

Wound biopsies were fixed in 4% paraformaldehyde then dehydrated in increasing concentrations of ethanol (50-100%). The dehydrated preparations were immersed first in xylene, then paraffin and xylene 1:1 solution, then in pure melted paraffin (60° C.). The paraffin blocks were then sectioned by a microtome and the sections were mounted on Super Frost™ slides.

(vii) H&E Staining.

Paraffin embedded wound-section slides were incubated at 60° C. for 60 minutes and were de-parafinated by washing the slides twice with toluene (100%) for 10 minutes, then rehydrated in decreasing concentration of ethanol (100-50%) for 5 minutes each. The slides were stained with hematoxylin (ready to use solution) for 10 minutes, rinsed with water, stained with eosin (0.5% in DDW) for 5 minutes, and then washed with 70% ethanol by 2 quick immersions. Thereafter, the slides were dehydrated by washing once with 95% ethanol for 2 minutes, twice with 100% ethanol for 5 minutes, and twice with xylene (100%) for 10 minutes, then mounted with entellan (MERCK Darmstadt Germany).

(viii) Keratin 1 and Keratin 14 Staining.

Paraffin embedded wound-section slides were de-parafinated as described for H&E staining above and incubated in blocking solution (5% BSA and 0.5% Tween 20™ in PBS) for 1 hour. The slides were then incubated with either anti-keratin 1 (1:500) or anti-keratin 14 (1:1000) antibody in blocking solution (5% BSA and 0.5% Tween 20™ in PBS) at 4° C. overnight. Thereafter, the slides were washed five times with washing buffer (5% Tween 20™ in PBS for K14 and 0.5% Tween 20™ in PBS for K1) followed by incubation with biotinilated goat anti-rabbit antibody (ZYMED Laboratories Inc.) suspended (1:200) in blocking solution (5% BSA and 0.5% Tween 20™ in PBS) for 1 hour at room temperature. The slides were then washed three times with washing buffer (5% Tween 20™ in PBS) followed by incubation with an enzyme streptavidin conjugate in blocking solution (1:300) for 1 hour at room temperature. Thereafter, the slides were washed twice with washing buffer (5% Tween 20™ in PBS) for 5 minutes, once with PBS for 5 minutes and once with TRIS buffer (0.05 M in PBS) for 5 minutes, followed by incubation in DAB reagent for color development. The reaction was terminated by immersing the slides in double distilled water followed by counterstaining with eosin (ICN, 0.5% in DDW). The slides were then washed with 70% ethanol by 2 quick immersions; dehydrated by washing once again with 95% ethanol for 2 minutes, twice with 100% ethanol for 5 minutes, and twice with xylene (100%) for 10 minutes; and mounted with entellan (MERCK Darmstadt Germany).

Example 1

Figure 1:
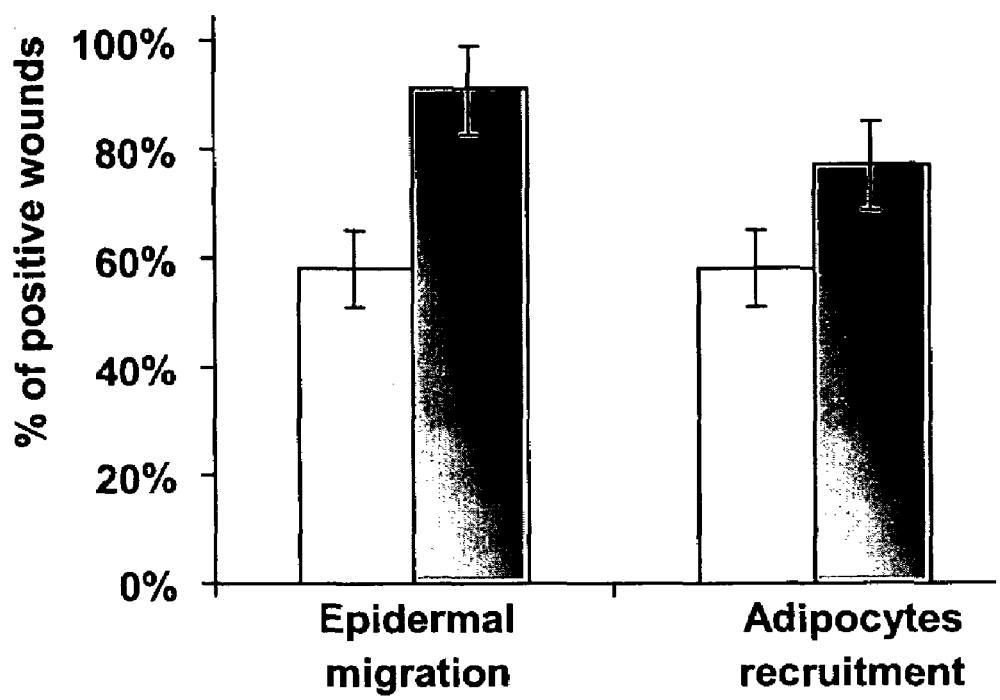
FIG. 1 illustrates the effect of insulin on adipocytes recruitment and epidermal cells migration at the wound area. Full thickness wounds were effected on the back of C57BL mice by incision. The wounds were treated daily with topical application of healing-inducing insulin (1 µM) for six days, then the mice were sacrificed and their wounds analyzed for epidermal cells migration and adipocytes recruitment. Epidermal cell migration was determined by K14 antibody staining and was considered positive if the wound was stained positive across the entire wound gap. Adipocytes recruitment was determined by H&E staining and was considered positive if adipocytes were detected inside the granulation tissue. The dark bars represent the insulin treatment and the light bars represent the buffer-treated control. The results are presented as percent of closed (positive) wounds and each bar represents the mean of six replications ± standard error.
Figure 2:
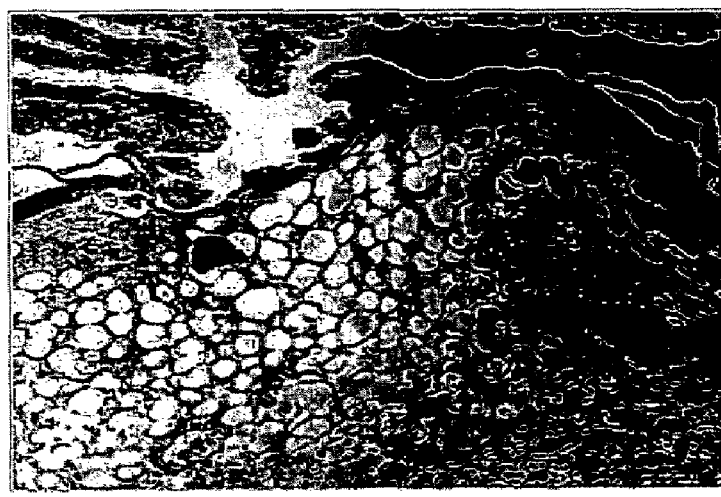
FIG. 2 is a histochemical micrograph illustrating the association of adipocytes with promotion of the wound healing process. Full thickness wounds were effected on the back of C57BL mice by incision. The mice were sacrificed seven days after wounding, then sectioned and stained with K14 antibody to highlight migrating epidermal cells. The micrographs show that recruited adipocytes are present at the wound gap in abundance during an early stage of the wound healing process. Magnification ×100.

Association of Adipocytes with Migrating Keratinocytes During the Wound Healing Process Migrating epidermal cells (keratinocytes) with recruited adipocytes were observed in 7-day-old wound tissue (FIG. 2). As can be seen in FIG. 1, migrating keratinocytes were observed across the wound gap in about 60% of the untreated wounds, and recruited adipocytes were also present in about 60% of the untreated wounds. FIG. 1 also shows that migrating keratinocytes and recruited adipocytes were observed in about 90% and 80% of insulin-treated wounds, respectively.

These results reveal that migration of keratinocytes to the wound gap area is closely associated with recruitment of adipocytes during an early stage of the wound healing process. The results thus indicate that migration of adipocytes to the wound area is involved in the wound healing process.

Example 2

The Effect of PPARγ Modulators on Keratinocytes Migration and Wound Contraction

Figure 3:
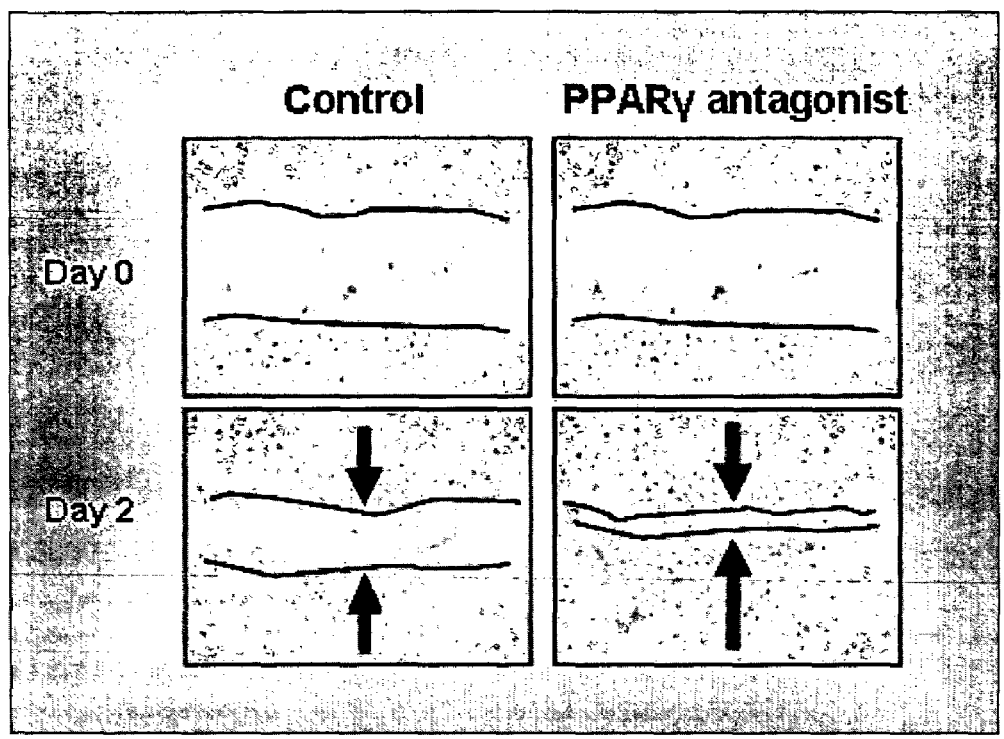
FIG. 3 illustrates the effect of a PPARγ antagonist (GW9662) on primary keratinocytes migration in vitro. Cultured keratinocytes were wounded (utilizing a 200 µm tip) and either untreated (control), or treated with 2 µM GW9662. The keratinocytes migration was observed under a light microscope. The upper panels show micrographs of pre-treated (Day 0) cultures, and the bottom left and panels show the resulting control and treated cultures, respectively (Day 2). The blue lines mark the edges of migrating keratinocytes and the arrows point out the enhanced migration of GW9662 treated cultures, as compared with the untreated control.
Figure 8:
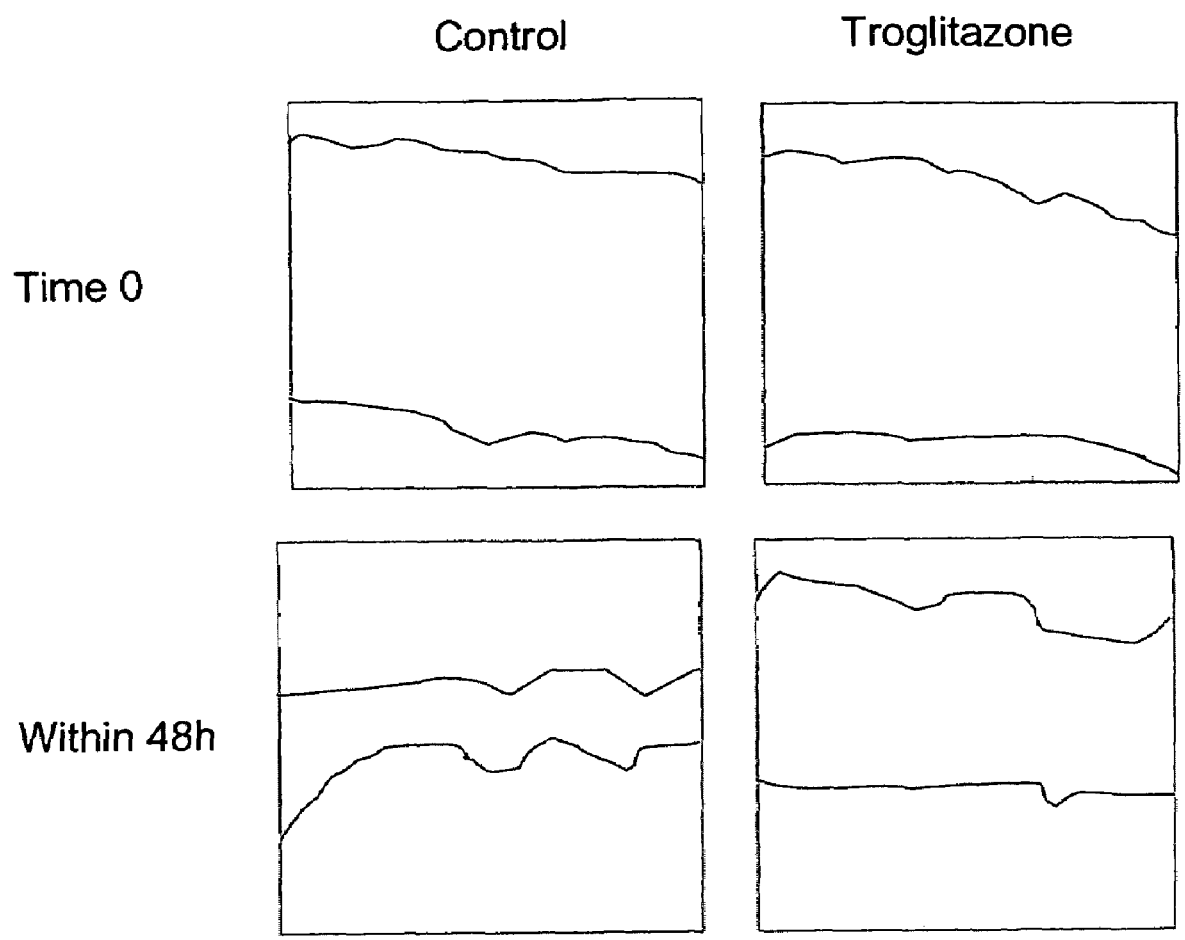
FIG. 8 illustrates the effect of a PPARγ agonist (troglitazone) on primary keratinocytes migration in vitro. Cultured keratinocytes were wounded (utilizing a 200 µm tip) and either untreated (control), or treated with 100 µM troglitazone, and their migration was observed under a light microscope. The upper panels (Time 0) show micrographs of pre-treated cultures, and the bottom left and right panels show the resulting control and treated cultures, respectively (within 48 hours). The lines mark the edges of cultured keratinocytes and indicate a substantially inhibited migration of cultured keratinocytes treated with troglitazone, as compared with the untreated control.

The effect of inhibiting or enhancing the activity of peroxisome proliferators-activated receptor gamma (PPARγ) on keratinocytes migration was evaluated utilizing the in vitro migration assay. Thus, primary keratinocytes were isolated and plated on 5 ml non-coated dishes until confluence in low $Ca^{2+}$ medium, and an artificial crossover scratch was formed in each dish with a 200 μm tip. Cells were either non-treated (control) or treated daily with PPARγ modulators. As can be seen in FIG. 3, the treatment of cultured primary murine keratinocytes with the PPARγ antagonist GW9662 promoted keratinocytes migration. On the other hand, the treatment of cultured keratinocytes with the PPARγ agonist troglitazone inhibited keratinocytes migration (FIG. 8).

Figure 4:
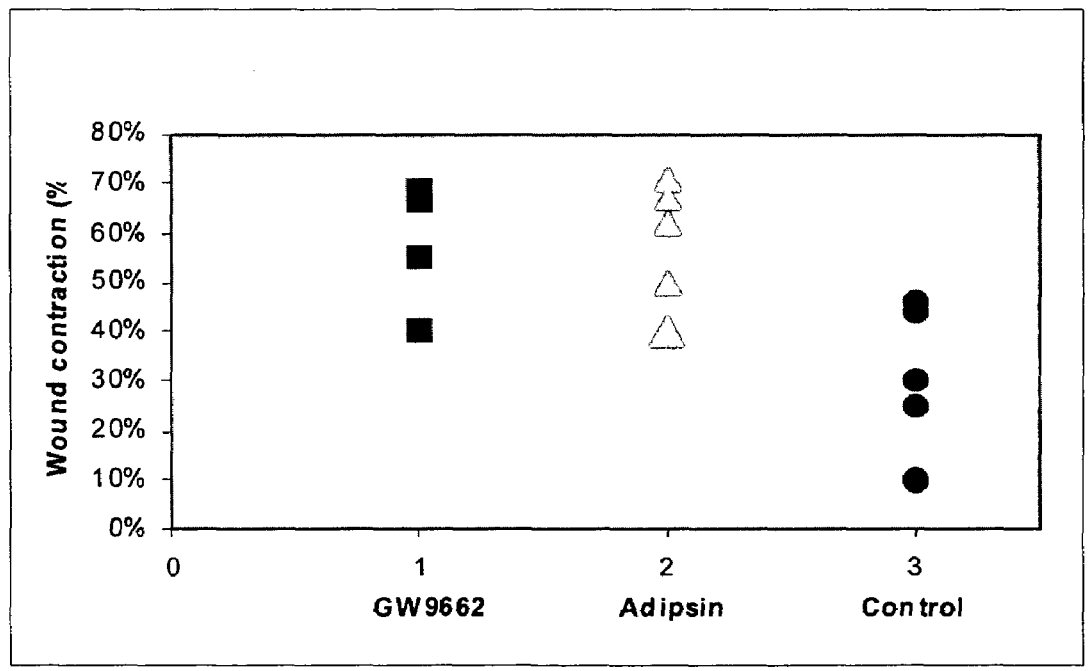
FIG. 4 is a graph illustrating the effects of a PPARγ antagonist (GW9662) and adipsin on wound healing in vivo. Full thickness wounds were effected on the back of C57BL mice by incision and the wounds were then measured (Day 0). The wounds were treated daily with topical application of PBS (control), adipsin 1 µM, or GW9662 2 µM for six days. Mice were then sacrificed and their wound areas were measured (Day 6). The portion of the wound area contracted after six days from the initial wound area was calculated (% wound contraction) for each treatment. The graph shows that both GW9662 and adipsin promoted a substantial wound contraction, as compared with the buffer-treated control.
Figure 5:
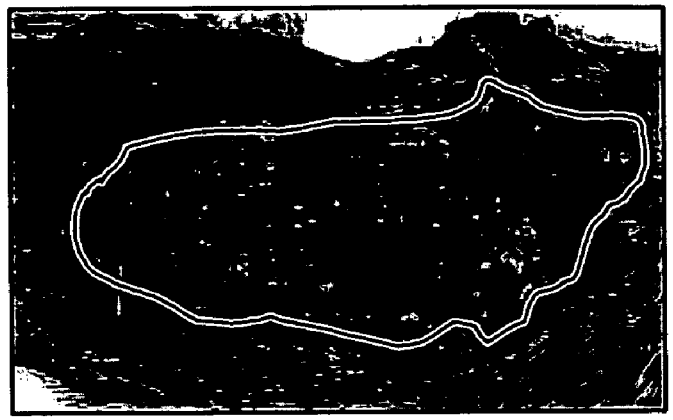
FIG. 5 is a morphological analysis illustrating the effects of a PPARγ antagonist (GW9662) and adipsin on wound closure in vivo. Full thickness wounds were effected on the back of C57BL mice by incision. The wounds were treated daily, for six days, with topical application of PBS (control), adipsin 1 µM, or GW9662 2 µM. The mice were then sacrificed, their wounds were fixed with paraformaldehyde and observed under a binocular microscope at ×5 magnification. The micrograph shows that the areas of wounds which were treated with GW9662, or with adipsin, are substantially smaller than the wound area of the buffer control.
Figure 5:
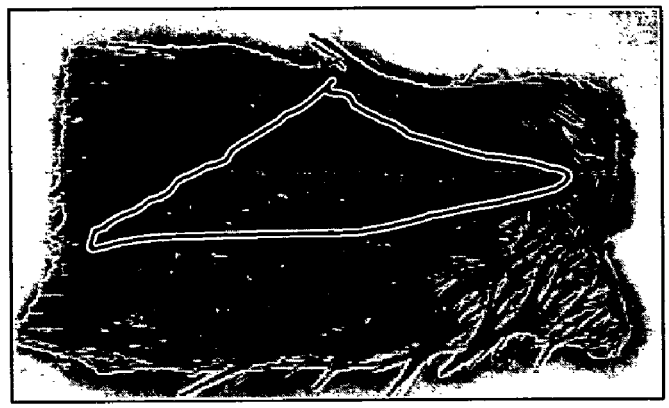
Figure 5:
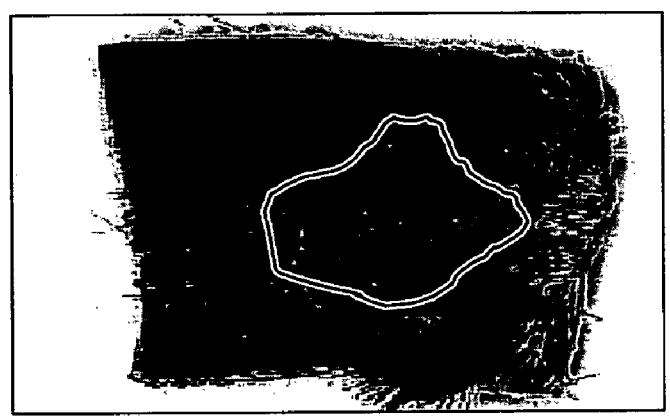
Figure 7:
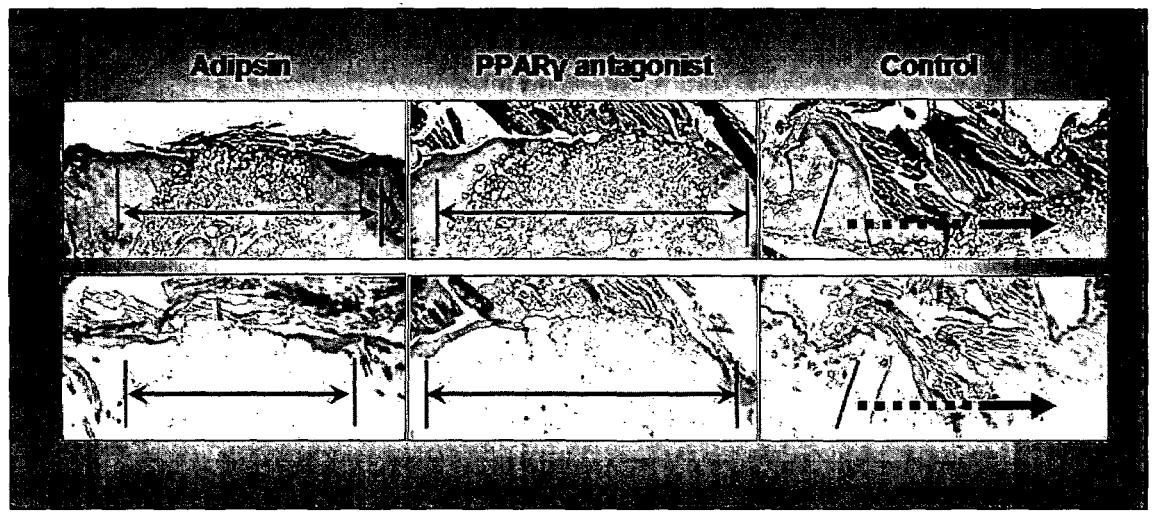
FIG. 7 is a histochemical micrograph illustrating the effects of a PPARγ antagonist (GW9662) and adipsin on epidermal migration and wound contraction. Full thickness wounds were effected on the back of C57BL mice by incision and were treated daily, for 6 days, with PBS (control), adipsin (1 µM) or GW9662 (2 µM). The treated mice were sacrificed six days after wounding. Histochemical wound sections were performed, stained with H&E (upper panel) or with K14 antibody (lower panel), and observed under a light microscope at ×50 magnification. The contraction was considered positive if both dermal wound sides (marked by black lines) could be observed in a single field. The open wound area in the untreated control (right) was too large to be contained in a single field (thus considered negative for dermal contraction), while the adipsin treated (left) and the GW9662 treated wounds (center) show positive dermal contraction. In addition, it is clearly observed that the epidermis in the adipsin treated and GW9662 treated groups is migrating toward covering the wound gap (K14 lower panels), whereas in the controls the epidermis is confined to the wound edges.
Figure 9:
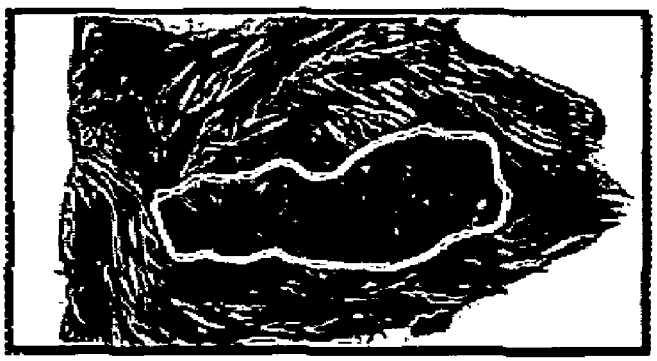
FIG. 9 is a morphological analysis illustrating the effects of insulin and a PPARγ agonist (troglitazone) on wound closure in vivo. Full thickness wounds were effected on the back of C57BL mice by incision and were treated daily, for 6 days, with topical application of PBS (control), insulin (10 nM), troglitazone (100 µM), or troglitazone (100 µM)+insulin (10 nM) combined. The mice were then sacrificed, their wounds were fixed with paraformaldehyde and observed under a binocular microscope at ×5 magnification. The micrograph shows that the insulin-treated wound area is substantially smaller than the buffer control, while the troglitazone and the troglitazone+insulin treated wounds are substantially larger than the buffer control.
Figure 9:
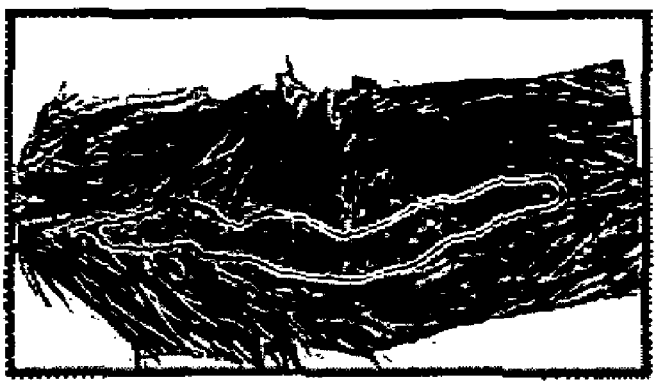
Figure 9:
Figure 9:
Figure 10:
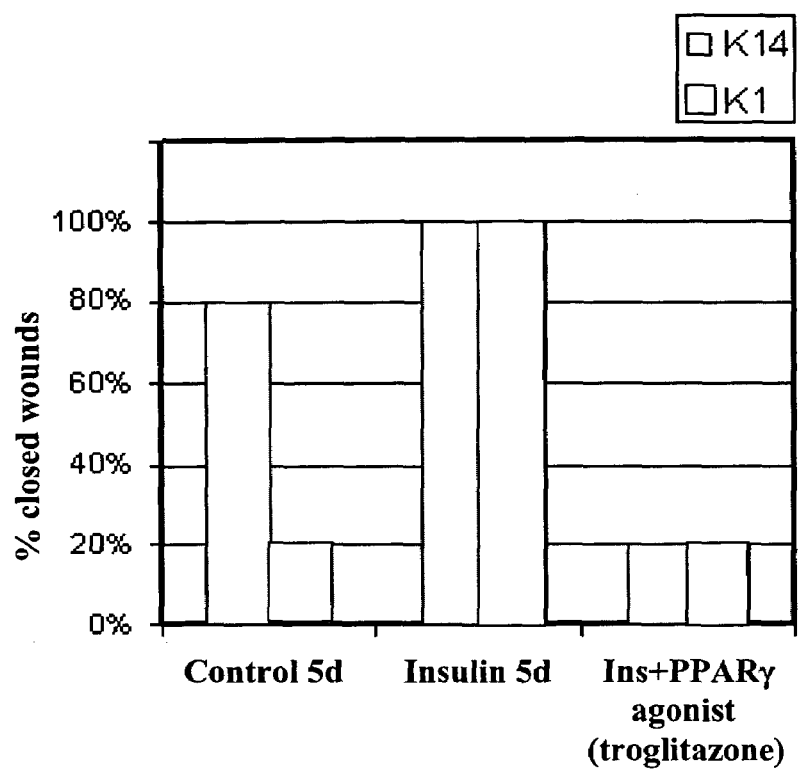
FIG. 10 illustrates the effect of insulin and a PPARγ agonist (troglitazone) on wound closure incidence. Full thickness wounds were effected on the back of C57BL mice by incision.

The effect of inhibiting or enhancing the activity of PPARγ using PPARγ antogonist and agonist, respectively, on wound healing was also evaluated in vivo. Accordingly, incision wounds were effected on the back of C57BL mice and were treated daily, for 6 days, with PBS buffer (control), or with various agents. The mice were sacrificed six days after wounding and the wounds were then analyzed. As can be seen in FIGS. 4-5, 7, the treatment with GW9662 (a PPARγ antagonist) promoted wound contraction and epidermal migration, as compared with the control. Contrary, a similar treatment with troglitazone (a PPARγ agonist) inhibited wound contraction (FIG. 9). Furthermore, troglitazone impaired insulin-induced wound healing (FIGS. 9-10).

Hence, the results clearly demonstrate that PPARγ agonist hinders the healing of wounds and that PPARγ antagonist (which attenuates PPARγ activity) can effectively promote the wound healing process. Accordingly, the results indicate that PPARγ antagonists, such as GW9662 can be used to effectively accelerate wound healing.

Example 3

The Effect of Adipsin on Keratinocytes Migration and Wound Contraction

Figure 6:
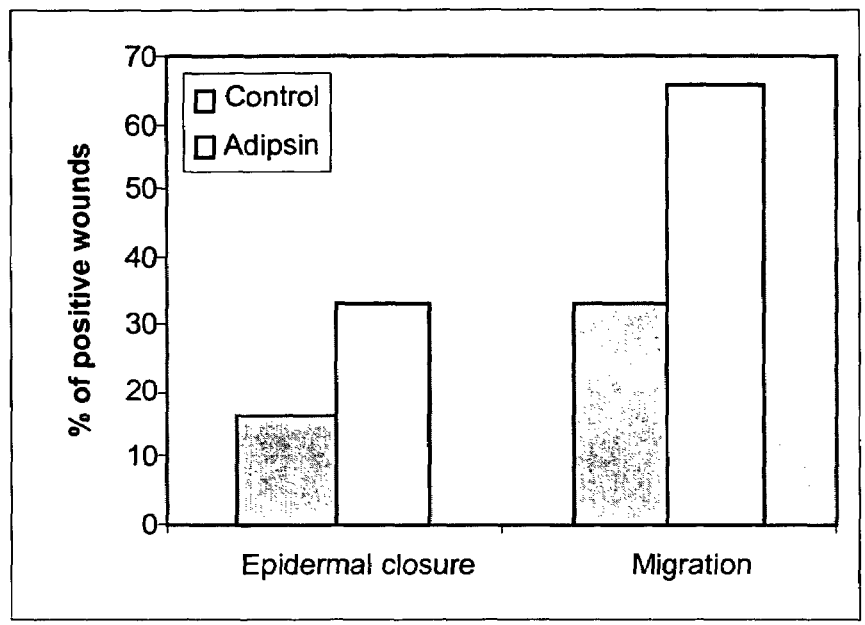
FIG. 6 illustrates the effect of adipsin on epidermal cell migration and wound closure. Full thickness wounds were effected on the back of C57BL mice by incision. The wounds were treated daily with topical application of either PBS (control) or adipsin 1 µM for seven days, then sacrificed, sectioned and analyzed for epidermal closure and migration by K14 antibody staining. Epidermal closure was considered positive if the wound was stained positive through the entire wound gap. Epidermal migration was considered positive if both wound edges were stained positive indicating progression across the wound gap rather than confined to the dermal walls. The bar graph shows that both epidermal closure and epidermal migration were markedly enhanced by adipsin. Each bar represents the mean of six replications.

The effect of adipsin (complementing Factor D, which is secreted from adipocytes) on wound healing was evaluated in vivo. Accordingly, full thickness incision wounds were effected on the back of C57BL mice and were treated daily, for 6 days, with PBS buffer (control), or with 1 μM adipsin. The mice were sacrificed 6 days after wounding and the wounds were then analyzed. As illustrated in FIGS. 4-5 and 7, adipsin substantially promoted wound contraction. In addition, adipsin increased epidermal closure from about 15% to about 30%, and increased keratinocytes migration from about 30% to about 65%, as compared with the buffer control (FIG. 6).

These results demonstrate that an adipokine, such as adipsin, can effectively induce or accelerate wound healing.

Example 4

Efficacy of Various Adipokines on Keratinocytes Migration In Vitro

Adipose tissue has recently gained the recognition as an endocrine organ. This endocrine entity is mostly associated to the visceral reserve; however, sub-cutaneous adipocytes have been shown to exert some endocrine activity. Based on these data and the data accumulated in our wound healing experiments, emphasizing the importance of adipocyte presence in the wound gap (see Example 1 above), we determined that adipocytes secrete pro-wound healing factors.

In order to test the effect of different adipokines on keratinocyte migration to close the wound gap, an in vitro scratch assay was used. Thus, primary keratinocytes were isolated and plated on 5 ml non-coated dishes until confluence in low $Ca^{2+}$ medium, and an artificial crossover scratch was formed in each dish with a 200 µm tip. Cells were either non-treated (control) or treated daily with insulin (0.1 unit/ml), hIL-4 (2 ng/ml), hIL-6 (0.2 ng/ml), leptin (4 µg/ml) or apelin (0.02 µg/ml or 0.2 µg/ml). Photo documentation was performed on day 0, 24 hrs and 48 hrs post treatment, and presented in FIG. 11.

The effect of each one of the adipokines on migration rate in keratinocytes was compared to the control and to the effect achieved by insulin, known to promote keratinocyte migration, as positive control. As shown in FIG. 11, it is clear that adipokines exert different effects on wound healing. The most prominent wound healing effect was exhibited in the IL-4- and apelin-treated groups (0.2 µg/ml) where keratinocyte migration was highly significant. Keratinocyte migration was observed also in the other treatment groups, namely IL-6, leptin and apelin (0.02 µg/ml), although not as significantly as in the IL-4- and apelin- (0.2 µg/ml) treated groups.

Both apelin and IL-4 were shown to be associated with downstream elements of the insulin signaling pathway and various protein kinases including PKC isoenzymes, which are known to effect proliferation and migration in various cell types.

From these results it may be concluded that adipokines may serve as positive therapeutic agents for wound healing, either as a single agent or in a formulation.

Example 5

The Effect of Various Adipokines on Fibroblasts Migration In Vitro

As shown in Example 4 above, adipokines influence keratinocyte migration in vitro thus promoting wound closure. However, when considering the in vivo model, adipokines' influence is not limited to the epidermal layer. The effect of different adipokines in wound healing in vitro assay (scratch assay) and in fibroblast migration and proliferation to close the wound gap, was tested. Fibroblast migration and proliferation have been implicated in the remodeling of the matrix in wounds.

Primary skin fibroblasts were isolated and plated on 5 ml non-coated dishes until confluence in low $Ca^{2+}$ medium, and an artificial crossover scratch was formed in each dish with a 200 µm tip. Cells were either non-treated (control) or treated with insulin (0.1 unit/ml), hIL-8 (5 ng/ml), hIL-1β (0.2 ng/ml), hIL-4 (2 ng/ml), apelin (0.2 µg/ml) or adiponectin (1 µg/ml); and collected after 24 hrs. Photo documentation was performed on day 0 and 24 hrs post treatment, and presented in FIG. 12.

The effect of each one of the adipokines on fibroblast-mediated wound healing was compared to the non-treated group as negative control and to the effect achieved by insulin, known to exert a prominent effect on fibroblasts in vitro, as positive control and a reference point of efficacy. As shown in FIG. 12, IL-1, apelin and adiponectin have all promoted fibroblasts migration to completely close the wound gap. IL-8 had a smaller yet significant effect in comparison to the non-treated group. However, IL-4 did not induce any additional effect compared to controls, indicating that it did not have a negative effect on the process.

It is important to point out that various adipokines exert different signaling mechanisms in different cell types, thus a positive effect on keratinocytes does not imply a similar effect on fibroblasts. This conclusion is well supported by the IL-4 that was found to induce keratinocyte migration (see Example 4 above) but does not have the same effect on fibroblasts. This does not mean that IL-4 is not suitable for treating wounds in vivo; however, it does implicate the signaling pathway involved in each cell type.

From this assay we conclude that specific adipokines such as apelin and adiponectin exhibit prominent effects on wound healing. These data emphasize the need in further investigation and determination of the mechanism by which we will be able to regulate wound healing process via specific adipokines, thus promoting new potential therapeutic agents for single or formulation applications.

Example 6

The Effect of Visfatin on Wound Healing In Vitro

Visfatin has recently been shown in the literature as an insulin-mimetic hormone (activation of insulin receptor has been observed in visfatin concentration range between 0.01 µg/ml to 10 µg/ml) secreted from visceral adipose tissue and its role in glucose metabolism exhibits insulin like regulation in various metabolic tissues such as liver, muscle and adipocytes. Moreover, visfatin has been shown to be secreted, to a lesser extent, from sub-cutaneous fat as well, and it is this entity that encouraged us to enroll it in the adipokine related wound healing formulations.

Methods (i) Keratinocytes/Fibroblasts Scratch Migration Assay.

Primary keratinocytes/fibroblasts were isolated and plated on 5 ml non-coated dishes until confluence in low $Ca^{2+}$ medium, and an artificial cross-over scratch was formed in each dish with a 200 µm tip. Then, cells were either non-treated or treated with visfatin (0.1 µg/ml or 0.01 µg/ml) or insulin (0.1 unit/ml) for up to 48 hrs. Photo documentation was performed at day 0, 24 and 48 hrs post treatment, and presented in FIGS. 13, 18.

(ii) Western Blot Analysis for Proliferation and Differentiation Markers.

Primary keratinocytes were isolated, plated on 100 mm tissue dishes and maintained for 5 days in medium with low $Ca^{2+}$ (0.05 mM) until 80% confluence. Then, cells were either non-treated (control) or treated with insulin (0.1 unit/ml, 1 µM) or visfatin (0.01 µg/ml or 0.1 µg/ml). 24 hrs post treatment cells were lyzed and analyzed for PCNA expression by western blot analysis. The results are presented in FIG. 14.

(iii) Thymidine Incorporation Assay.

Primary keratinocytes were isolated, plated on 6 well tissue dishes and maintained for 5 days in medium with low $Ca^{2+}$ (0.05 mM) until 80% confluence. Then, cells were either non-treated (control) or treated with visfatin (0.1 µg/ml or 0.01 µg/ml) for 24 hrs. 6 hrs post treatment $Ca^{2+}$ mM was added to the medium, and the next day, cells were pulsed with [$^3$H]thymidine (1 uCi/ml) for 1 hour. After incubation, cells were washed three times with PBS and 5% trichloroacetic acid (TCA) was added into each well for 1 hour. The solution was then removed and cells were stabilized in 1M NaOH. The labeled thymidine incorporated into the cells was counted in a ³H-window of a Tricarb liquid scintillation counter. The results are presented in FIG. 15.

(iv) Differentiation Assay for Keratin 1.

Primary keratinocytes were isolated, plated on 100 mm tissue dishes and maintained for 5 days in medium with low $Ca^{2+}$ (0.05 mM) until 80% confluence. Then, cells were either non-treated (control) or treated with insulin (0.1 unit/ml, 1 µM) or visfatin (0.01 µg/ml or 0.1 µg/ml). 24 hrs post treatment cells were lysed and analyzed for K1 (Keartin 1) expression by western blot analysis. The results are presented in FIG. 16.

(v) Differentiation Assay for Filaggrin.

Primary keratinocytes were isolated, plated on 100 mm tissue dishes and maintained for 5 days in medium with low $Ca^{2+}$ (0.05 mM) until reaching 80% confluence. Then, cells were either non-treated (control) or treated with visfatin (0.01 µg/ml or 0.1 µg/ml). Terminal differentiation was induced by adding $Ca^{2+}$ to the medium 6 hrs post treatment. 24 hrs post treatment cells were lysed and analyzed for filaggrin expression by western blot analysis. The results are presented in FIG. 17.

Results

The role of visfatin on wound healing in vitro was first examined in the scratch migration assay. The influence of visfatin on keratinocytes by expression of proliferation and differentiation markers, was then assessed both by western blot for expression of proliferating nuclear antigen protein (PCNA) and by thymidine incorporation assays.

As shown in FIG. 13, visfatin does not halt or interfere with migration of keratinocytes, relative to controls. The higher concentration of visfatin (0.1 µg/ml) induced migration in keratinocytes though not significantly. Concomitantly, as further shown in FIG. 14, the lower concentration of visfatin (0.01 µg/ml) significantly decreased PCNA expression levels in keratinocytes, indicating that it has a more potent ability to inhibit cell proliferation. This result is further supported by the thymidine incorporation measurement assay, demonstrated in FIG. 15; indicating a dose dependent inhibition of proliferation where the lower dose (0.01 µg/ml) exhibited lower thymidine incorporation than the higher dose (0.1 µg/ml) and controls. In the conditions promoting cell differentiation ($Ca^{2+}$ 0.12 mM addition to the medium), visfatin inhibited even further the proliferation rate of these cells.

Expression of differentiation markers in response to visfatin was assessed utilizing western blot analysis of Keratin-1 and filaggrin. Both proteins are representatives of the keratin filament network present in keratinocytes. Keratin-1 (K1) is expressed when cells from the epidermal basal layer differentiate into the spinous layer keratinocytes. Filaggrin is expressed in terminal differentiation stages when spinous cells transform into the granular cell layer.

FIGS. 16-17 demonstrate that visfatin promotes keratinocyte differentiation primarily terminal differentiation, both in respect to non treated cells as well as to cells treated with insulin, that has been shown to promote keratinocyte proliferation, thus lowering expression of differentiation markers. Visfatin treated cells express both Keratin 1 (spinous layer marker) and the terminal differentiation filaggrin. It is the marked elevation in filaggrin levels, in both active doses, that promotes our understanding of the differences between insulin and visfatin as well as the physiological and patho-physiological implications of visfatin treatment.

Following the complex wound healing model system we tested the influence of visfatin on fibroblasts migration and proliferation, utilizing the in vitro Fibroblasts migration scratch assay.

FIG. 18 shows the differential effects of visfatin and insulin on the different cell types associated with wound healing. As can be seen, treating primary skin fibroblasts with visfatin promotes fibroblast migration and proliferation to the extent of insulin treatment, contrary to the result presented in FIG. 13, where no effect was exhibited in keratinocyte migratory potential.

Our data indicate that visfatin at concentration range between 0.01 µg/ml and 0.1 µg/ml can be utilized for modulation of skin cells. However, since insulin receptors have been previously shown to be activated by visfatin at concentration range between 0.01 µg/ml to 10 µg/ml, it may be concluded that skin cells modulation may be induced utilizing higher concentrations (up to 10 µg/ml) of visfatin as well.

The results described above indicate that visfatin influences keratin differentiation together with matrix remodeling typical for late wound healing stages, suggesting that visfatin might play a role in overcoming aesthetic complications of skin such as keloid and hypertrophic scarring. These results further suggest that visfatin might be beneficial in treatment of hyperplastic proliferative skin disorders.

Example 7

The Effect of Adiponectin and Visfatin on Wound Healing In Vivo

In light of previous results, demonstrating adipokines effects on wound healing in vitro, we conducted an in vivo study.

Full thickness 20 mm incision wounds were performed on 8-10 week old C57BL mice, 6 mice per group. The wounds were treated daily for 7 days with PBS (control), adiponectin (1 µg/ml) or visfatin (0.01 µg/ml). Skin biopsies were paraffin embedded and slide sections representing the widest area of the wound were prepared. Sections were then subjected to histochemical staining such as H&E and Masson Trichrome (collagen).

As shown in FIG. 19, the adiponectin treated groups presented better healing parameters according to our wound healing assessment protocol, as presented by epidermal closure, dermal contraction and matrix remodeling (represented by the collagen deposition in the wound gap), thus proving the potential of adiponectin as a therapeutic agent for wound healing either as a single agent or as a part of a formulation. As further shown in FIG. 19, visfatin attracts adipocytes to the wound site and reduces inflammation. In light of our previous in vitro studies indicating that visfatin promotes keratinocyte terminal differentiation (see Example 6 hereinabove), it is concluded that visfatin might be beneficial in late wound healing stages and resolving aesthetic skin disorders.

Based on the results presented above, together with previous data, it is concluded that different adipokines affect different signaling mechanisms in skin, promoting specific manipulation on different stages in the wound healing process.

Example 8

The Effect of Adipocyte Derived Factors and Adipocytes Homogenates on Wound Healing In Vivo Adipocyte involvement in the wound healing process has been proven beneficial in our in vitro and ex-vivo studies. In light of these results we conducted a series of in vivo experiments to test the influence of adipocytes and adipocytes secretions on wound healing process in live animal models.

Full thickness 20 mm incision wounds were performed on 8-10 week old C57BL mice, 6 mice per group. The wounds were treated daily, for 5 days, either with PBS (control), adipokines collected from the secretion of human visceral primary preadipocytes, adipokines collected from the secretion of human sub-cutaneuos primary preadipocytes, homogenized cell extract from human sub-cutan layer or homogenized cell extract from human lipo-suction. Morphological assessment was performed daily utilizing photo documentation.

FIG. 20 shows the average wound size in mice from each treatment 5 days post wounding. The morphological assessment clearly demonstrates the positive effect of treatment with adipocytes as well as various adipocyte derived factors on wound healing. All treatments induced wound healing better than controls; wounds appear smaller and the scab is lighter indicating a more progressed stage in wound healing. Based on these results, and since morphological analysis is the primary parameter utilized in wound healing in vivo as well as in humans, it is concluded that adipocyte derived factors as wells as adipocytes as homogenates might be efficient in treating wounds as a topical or formulated therapeutics.

Example 9

The Effect of Adipocytes and Adipokines on Human Skin Wound Healing in the CAM Ex-Vivo Model System It is a well known fact that animal model studies are not always an accurate indication of human bio-physiology. Therefore, in our studies of skin and wound healing we utilized a method overcoming this difficulty, designated the chick chorioallantioic membrane (CAM) ex-vivo model system.

The chick chorioallantioic membrane (CAM) is a highly vascularised tissue responsible for gas exchange, which has been reported as a grafting platform of various tissues for testing drug therapies, angiogenesis or other developmental processes (Maas et al., 1999). Using the CAM ex-vivo model system enabled us to implant human skin explants, inflict a wound and test various wound healing agents, overcoming the differences in skin structure and physiology between animal models (usually mice) and human skin. Two days post grafting, the skin obtains its own supply of blood vessels, which allow graft maintenance for a period of up to 12 days.

Skin biopsies were obtained from a human abdominal source with the underlying hypodermis layer. The skin was sectioned into circular pieces of 1.5 cm diameter×1 cm explants and grafted on 8-9 old fertilized eggs that were incubated in 37° C. wet and rotated every 4 hrs.

Skin wounds range in size, depth and types, thus we studied full thickness as well as partial thickness wounds, utilizing a 6 mm punch, simulating specific wound populations. Prior to grafting, the CAM was slightly injured, just enough to induce a minor bleeding that enables the skin to be implemented into the CAM. Wounds were treated daily, for 5 days, with 20 µl of either PBS (control), adipokines collected from the secretion of human visceral primary preadipocytes, adipokines collected from the secretion of human sub-cutaneuos primary preadipocytes, homogenized autologous cell extract from sub-cutan layer or homogenized autologous cell extract from lipo-suction. Morphological assessment was performed daily utilizing photo documentation under binocular.

FIG. 21 shows the effect of adipocytes and adipokines on human skin wound healing in the CAM ex-vivo model system, by presenting full and partial thickness wounds treated with various adipocyte derived factors, either secreted (adipokines) or extracted from cell homogenate. The results demonstrated that treatment with adipokines promoted wound closure compared to control (PBS) groups. From the results presented, it is clear that adipocytes related factors, both visceral and sub-cutan origins, collected from primary cell cultures, play a crucial role in the wound healing process in human skin. Similar results were exhibited in the partial wounded skin treated with adipocyte homogenates.

Based on these results, we conclude that adipocytes and their derived factors induce unique mechanisms in human skin physiology and wound healing. Recognizing the specific factors and or cell population type promoting quality wound healing in human skin can provide the platform for developing protocols for wound healing and/or potential therapeutic agents, specifically, formulation comprised of adipocyte derived factors or an autologous adipocyte transplant (signified in the cell homogenate treated groups).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications and sequences identified by their name and/or database accession numbers mentioned in this specification are herein incorporated in their entirety by reference into the specification, to the same extent as if each individual publication, patent, patent application or sequence was specifically and individually indicated to be incorporated herein by reference. In addition, citation or identification of any reference in this application shall not be construed as an admission that such reference is available as prior art to the present invention.

REFERENCES

Ausubul, F. M. et al., Current Protocols in Molecular Biology, Greene Publishing Associates, 1989

Chang et al., Somatic Gene Therapy, CRC Press, Ann Arbor, Mich. (1995)

Digby, J. E. Montague, C. T. Sewter, C. P. Sanders, L. Wilkison, W. O. O'Rahilly, S. Prins, J. B., Thiazolidinedione exposure increases the expression of uncoupling protein 1 in cultured human preadipocytes, *Diabetes,* 1998, 47, 138-141

Emerson, S. G., Ex vivo expansion of hematopoietic precursors, progenitors, and stem cells: the next generation of cellular therapeutics, *Blood,* 1996, 87, 3082-3088

Fingl et al., in "The Pharmacological Basis of Therapeutics", Ch. 1 p. 1 1975

Freshney, R. I., Culture of Animal Cells, 1994, $3^{rd}$ Ed., 310-312

Fuchs, E., Epidermal differentiation: the bare essentials, *J. Cell Biol.,* 1990, 111, 2807-2814

Gilboa et al., Transfer and Expression of Cloned Genes Using Retroviral Vectors, *BioTechniques,* 1986, 4, 504-512

Hauner, H. Entenmann, G. Wabitsch, M. Gaillard, D. Ailhaud, G. Negrel, R. Pfeiffer, E. F., Promoting effect of glucocorticoids on the differentiation of human adipocyte precursor cells cultured in a chemically defined medium, *J Clin Invest*, 1989, 84, 1663-1670

Hennings, H. Holbrook, K. A., Calcium regulation of cell-cell contact and differentiation of epidermal cells in culture. An ultrastructural study, *Exp. Cell Res.*, 1983, 143, 127-142

Hennings, H. Michael, D. Cheng, C. Steinert, P. Holbrook, K. Yuspa, S. H., Calcium regulation of growth and differentiation of mouse epidermal cells in culture, *Cell*, 1980, 19, 245-254

Hunt, T. K. Goodson, W. H., "Wound Healing," in Way, L. W. (ed.), Current Surgical Diagnosis and Treatment, Appleton & Lange (Norwalk, 1988), 86-98

Kiritsy, C. P. Lynch, B. Lynch, S. E., Role of growth factors in cutaneous wound healing: a review, *Crit. Rev. Oral Biol. Med.*, 1993, 4, 729-760

Lej et al., *J. Bacteriol.*, 1987, 169, 4379

Maas, J. W. Le Noble, F. A. Dunselman, G. A. de Goeij, A. F. Struyker Boudier, H. A. Evers, J. L., The chick embryo chorioallantoic membrane as a model to investigate the angiogenic properties of human endometrium, *Gynecol Obstet Invest.*, 1999, 48, 108-112

Michalnik et al., Impaired skin wound healing in peroxisome proliferator-activated receptor (PPAR)alpha and PPAR-beta mutant mice, *J. Cell Biol.* 2001, 154, 799-814

Miller, A. D., Progress toward human gene therapy, *Blood*, 1990, 76, 271-278

Rangwala, S. M. Lazar, M. A., Transcriptional control of adipogenesis, *Annu. Rev. Nutr.* 2000, 20, 535-559

Reubinoff, B. E. Pera, M. F. Fong, C. Y. Trounson, A. Bongso, A., Embryonic stem cell lines from human blastocysts: somatic differentiation in vitro, *Nature Biotechnology*, 2000, 18, 399-404

Rodbell, M. Krishna, G., Preparation of isolated fat cells and fat cell "ghosts"; methods for assaying adenylate cyclase activity and levels of cyclic AMP, *Methods Enzymol.*, 1974, 31, 103-114

Rodriguez, R. L. Denhardt, D. T. (ed.), Vectors, a survey of molecular cloning vectors and their uses, Butterworths Boston, 1988

Russel, W. C., *J. Gen. Virol.*, 2000, 81, 57-63

Sambrook et al., Molecular Cloning: A Laboratory Manual, Cold Springs Harbor Laboratory, New York (1989, 1992).

Seth, P., Katayose, Y. Rakkar, A. N. S., Adenoviral vectors for cancer gene therapy, In P. Seth (ed.), Adenoviruses: basic biology to gene therapy, R. G. Landes Co., Austin, Tex, 1999, 103-120

Singer, A. J. Clark, R. A., Cutaneous wound healing. *N. Engl. J. Med.*, 1999, 341, 738-746

Tennenbaum, T. Li, L. Belanger, A. J. De Luca, L. M. Yuspa, S. H., Selective changes in laminin adhesion and α6β4 integrin regulation are associated with the initial steps in keratinocyte maturation, *Cell Growth Differ.*, 1996a, 7, 615-628

Tennenbaum, T. Belanger, A. J. Quaranta, V. Yuspa, S. H., Differential regulation of integrins and extracellular matrix binding in epidermal differentiation and squamous tumor progression, *J. Invest. Dermatol.*, 1996b, 1, 157-161

Van Epps, D. E. Cender, J. Lee, W. Schilling, M. Smith, A. Smith, S. Unverzagt, K. Law, P. Burgess, J., Harvesting, characterization, and culture of CD34+ cells from human bone marrow, peripheral blood, and cord blood, *Blood Cells*, 1994, 20, 411-423

Vega et al., Gene Targeting, CRC Press, Ann Arbor, Mich. (1995)

Von Heijne, G., Signal Sequences: The Limits of Variation, *J. Mol. Biol.*, 1985, 184, 99-105

Wabli W., *Swiss Med. Wkly.*, 2002, 132, 81-82

Weinstein, M. L., Update on wound healing: a review of the literature, *Mil. Med.*, 1998, 163, 620-624

Whitby, D. J. Ferguson, M. W., Immunohistochemical localization of growth factors in fetal wound healing, *Dev. Biol.*, 1991, 147, 207-215

Yuspa, S. H. Kilkenny, A. E. Steinert, P. M. Roop, D. R., Expression of murine epidermal differentiation markers is -tightly regulated by restricted extracellular calcium concentrations in vitro, *J. Cell Biol.*, 1989, 109, 1207-1217

Yuspa, S. H., The pathogenesis of squamous cell cancer: lessons learned from studies of skin carcinogenesis—Thirty-third G. H. A. Clowes Memorial Award Lecture. *Cancer Res.*, 1994, 54, 1178-1189

The invention claimed is:

1. A method of inducing or accelerating a healing process of a damaged skin or skin wound, the method comprising administering to the skin cells colonizing the damaged skin or skin wound area a therapeutically effective amount of adipsin to induce or accelerate the healing process of the damaged skin or skin wound.

2. The method of claim 1, wherein said, skin wound is selected from the group consisting of an ulcer a diabetes-related wound, a burn, a sun burn, an aging skin wound, a corneal ulceration wound, an inflammatory gastrointestinal tract disease wound, a bowel inflammatory disease wound, a Crohn's disease wound, an ulcerative colitis wound, a hemorrhoid, an epidermolysis bulosa wound, a skin blistering wound, a psoriasis wound, an animal skin wound, a proud flesh wound, an animal diabetic wound, a retinopathy wound, an oral wound (mucositis), a vaginal mucositis wound, a gum disease wound, a laceration, a surgical incision wound and a post-surgical adhesion wound.

3. The method of claim 2, wherein said ulcer is selected from the group consisting of a diabetic ulcer, a pressure ulcer, a venous ulcer, a gastric ulcer and an HIV-related ulcer.

4. The method of claim 1, wherein the at least one agent administered comprises adipsin in combination with at least one agent selected from the group consisting of adiponectin, apelin, visfatin, lipoprotein lipase, plasminogen activator inhibitor-1 (PAI-1), IL-4, IL-8, angiotensin I, angiotensin II, angiotensin III, angiotensin IV, cycloanalogs of angiotensin I, cycloanalogs of angiotensin II, cycloanalogs of angiotensin III, cycloanalogs of angiotensin IV, angiotensinogen, 1-butyrylglycerol, matrix metalloproteinase 2, matrix metalloproteinase 9, and a PPAR-γantagonist.

5. A method of inducing or accelerating a healing process of a damaged skin or skin wound, the method comprising administering to the skin cells colonizing the damaged skin or skin wound area a therapeutically effective amount of adipsin and visfatin thereby inducing or accelerating the healing process of the damaged skin or skin wound.

6. The method of claim 5, wherein said skin wound is selected from the group consisting of an ulcer, a diabetes-related wound, a burn, a sun burn, a aging skin wound, a corneal ulceration wound, an inflammatory gastrointestinal tract disease wound, a bowel inflammatory disease wound, a Crohn's disease wound, an ulcerative colitis wound, a hemorrhoid, an epidermolysis bulosa wound, a skin blistering wound, a psoriasis wound, an animal skin wound, a proud flesh wound, an animal diabetic wound, a retinopathy wound, an oral wound (mucositis), a vaginal mucositis wound, a gum disease wound, a laceration, a surgical incision wound and a post-surgical adhesion wound.

7. The method of claim 6, wherein said ulcer is selected from the group consisting of a diabetic ulcer, a pressure ulcer, a venous ulcer, a gastric ulcer and an HIV-related ulcer.

8. The method of claim 5, wherein the adipsin and visfatin are contained in a pharmaceutical composition adapted for topical or subcutaneous administration.

9. The method of claim 8, wherein the pharmaceutical composition comprises at least one formulation selected from the group consisting of an aqueous solution, a gel, a cream, a paste, a lotion, a spray, a suspension, a powder, a dispersion, a salve and an ointment.

10. The method of claim 9, wherein the pharmaceutical composition comprises a solid support.

11. A method for increasing the closure of a wound on animal comprising the steps of:

a) providing a pharmaceutical composition comprising adipsin; and
b) topically administering to a wound on an animal an effective amount of the pharmaceutical composition;
whereby closure of the wound is increased.

12. The method of claim 11 wherein the pharmaceutical composition comprises an aqueous solution.

13. The method of claim 12, wherein the pharmaceutical composition comprises at least one formulation selected from the group consisting of a gel, a cream, a paste, a lotion, a spray, a suspension, a powder, a dispersion, a salve and an ointment.

14. The method of claim 13, wherein the pharmaceutical composition comprises a solid support.

* * * * *

UNITED STATES PATENT AND TRADEMARK OFFICE
CERTIFICATE OF CORRECTION

PATENT NO. : 7,638,484 B2
APPLICATION NO. : 11/348527
DATED : December 29, 2009
INVENTOR(S) : Braiman-Wiksman et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 178 days.

Signed and Sealed this

Twenty-first Day of December, 2010

David J. Kappos
*Director of the United States Patent and Trademark Office*